(12) United States Patent
Mao et al.

(10) Patent No.: US 11,841,365 B2
(45) Date of Patent: Dec. 12, 2023

(54) DEVICES, KITS, AND METHODS FOR LABEL-FREE FOCUSING AND/OR SEPARATION OF SUB-MICRON PARTICLES

(71) Applicant: University of Georgia Research Foundation, Inc., Athens, GA (US)

(72) Inventors: Leidong Mao, Watkinsville, GA (US); Yang Liu, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 276 days.

(21) Appl. No.: 16/930,664

(22) Filed: Jul. 16, 2020

(65) Prior Publication Data

US 2021/0018499 A1  Jan. 21, 2021

Related U.S. Application Data

(60) Provisional application No. 62/874,941, filed on Jul. 16, 2019.

(51) Int. Cl.
*G01N 33/543* (2006.01)
*B01L 3/00* (2006.01)
*G01N 15/14* (2006.01)
*G01N 15/10* (2006.01)

(52) U.S. Cl.
CPC .... *G01N 33/54366* (2013.01); *B01L 3/50273* (2013.01); *B01L 3/502753* (2013.01); *B01L 3/502761* (2013.01); *G01N 15/1404* (2013.01); *G01N 15/1484* (2013.01); *B01L 2200/0647* (2013.01); *B01L 2400/043* (2013.01); *G01N 2015/1006* (2013.01); *G01N 2015/149* (2013.01); *G01N 2015/1415* (2013.01); *G01N 2015/1486* (2013.01)

(58) Field of Classification Search
None
See application file for complete search history.

(56) References Cited

U.S. PATENT DOCUMENTS

| | | | |
|---|---|---|---|
| 2012/0080360 A1* | 4/2012 | Stone | B03C 1/01 210/695 |
| 2016/0123858 A1* | 5/2016 | Kapur | B01L 3/502753 73/61.71 |
| 2017/0038285 A1* | 2/2017 | Zheng | B01L 3/502707 |

OTHER PUBLICATIONS

Nam et al. (Continuous separation of microparticles in a microfluidic channel via the elasto-inertial effect of non-Newtonian fluid. Lab on a Chip 12.7 (2012): 1347-1354) (Year: 2012).*
Woo, et al., "Exodisc for Rapid, Selective, and Efficient Isolation and Analysis of Nanoscale Extracellular Vesicles from Biological Samples", ACS Nano; 2017 American Chemical Society.
(Continued)

*Primary Examiner* — Christopher L Chin
(74) *Attorney, Agent, or Firm* — Thomas | Horstemeyer, LLP

(57) ABSTRACT

The present disclosure provides devices, kits, and methods for focusing/enriching and/or separating/sorting submicron size particles, including biological entities such as exosomes and other submicron size extracellular vesicles. Devices, kits, and methods of the present disclosure utilize ferrohydrodynamic manipulation to focus populations of submicron particles into a stream for enrichment and/or further sort various sub-populations of submicron particles based on size differences.

8 Claims, 23 Drawing Sheets

(56) References Cited

OTHER PUBLICATIONS

Shin, et al. "Separation of extracellular nanovesicles and apoptotic bodies from cancer cell culture broth using tunable microfluidic systems", Scientific Reports; Apr. 28, 2017.

Xu, et al. "Magnetic-based microfluidic device for on-chip isolation and detection tumor-derived exosomes", Analytical chemistry; Anal. chem, 2018, 90.

Dong, et al. "Efficient isolation and sensitive quantification of extracellular vesicles based on an integrated ExoID-Dhip using photonic crystals", Lab on a Chip, Royal society of chemistry, 2019, 19.

Zhang, et al., "Ultrasensitive microfluidic analysis of circulating exosomes using a nanostructured graphene oxide/polydopamine coating", Lap on a Chip; Royal society of chemistry, 2016,16.

Zhao, et al. "Biocompatible and label-free separation of cancer cells from cell culture lines from white blood cells in ferrofluids", Lap on a Chip, Royal society of chemistry, 2017, 17.

Kanwar, et al. "Microfluidic device (ExoChip) for on-chip isolation, quantification and characterization of circulating exosomes", Lap on a Chip, Royal society of chemistry, 2014, 14.

Liang, et al. "An integrated double-filtration microfluidic device for isolation, enrichment and quantification of urinary extracellular vesicles for detection of bladder cancer", Scientific Reports, Apr. 2017.

Sunkara, et al. "Fully automated, label-free isolation of extracellular vesicles from whole blood for cancer diagnosis and monitoring", Theranostics 2019, vol. 9, Issue 7.

Zhang, et al. "Ultrasenstive detection of circulating exosomes with a 3D-nanopatterned microfluidic chip", Nature biomedical engineering, Jun. 2019, vol. 3.

Zhang, et al., "Asymmetric-flow field-flow fractionation technology for exomere and small extracellular vesicle separation and characterization", Nature protocols, Apr. 2019, vol. 14.

Chen, et al. "Microfluidic isolation and transcriptome analysis of serum mocrovesicles", Lab on a Chip, The Royal society of Chemistry, 2010, 10.

Wan, et al. "Rapid magnetic isolation of extracellular vesicles via lipid-based nanoprobes", Nature biomedical engineering, Apr. 10, 2017, vol. 1.

Hoshino, et al. "Tumour exosome integrins determine organotropic metastasis", Macmillan Publishers Limited, Nov. 19, 2015, vol. 527.

Wu, et al. "Isolation of exosomes from whole blood by integrating acoustics and microfluidics", PNAS, Oct. 3, 2017, vol. 114, No. 40.

Wang, et al., "Ciliated micropillars for the microfludic-based isolation of nanoscale lipid vesicles", Lab on a Chip, 2013, 13, 2879.

Shao, et al. "Chip-based analysis of exosomal MRNA mediating drug resistance in gliblastoma", Nature Communications, May 11, 2015.

Im, et al. "Lable-free detection and molecular profiling of exosomes with a nano-plasmonic sensor", Nature biotechnology, May 2014, vol. 32 No. 5.

Zhao, et al. "Tumor antigen-independent and cell size variation-inclusive enrichment of viable circulating tumor cells", Lap on a Chip, Royal society of chemistry, 2019.

Ashcroft, et al., "Determination of the size distribution of blood microparticles directly in plasma using atomic force microscopy and microfluidics", Biomed Microdevices, 2012.

Zhu, et la. "Continuous-flow ferrohydrodynamic sorting of particles and cells in microfluidic devices", Microfluid Nanofluid, 2012.

Wunsch, et al. "Nanoscale lateral displacement arrays for the separation of exosomes and colloids down to 20 nm", Nature nanotechnology, Aug. 2016.

Liu, et al. "Field-free isolation of exosomes from extracellular vesicles by microfluidic viscoelastic flows", ACS Nano, 2017 American Chemical Society.

Peinado, et al., "Melanoma exosomes educate bone marrow progenitor cells toward a pro-metastatic phenotype through MET", Nature Medicine, May 2012.

Zhao, et al., "Label-free ferrohydrodynamic cell separation of circulating tumor cells", Lab on a Chip., Royal society of chemistry, 2017.

Liu, et al., "The exosome total isolation chip", ACS Nano 2017.

* cited by examiner

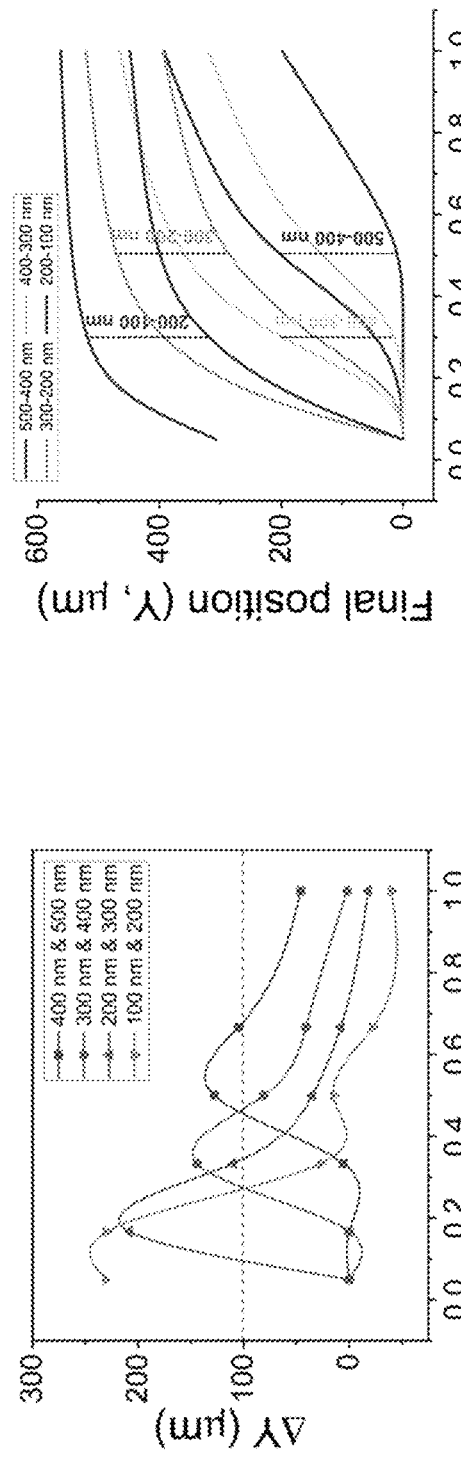
*FIG. 7A*
*FIG. 7B*
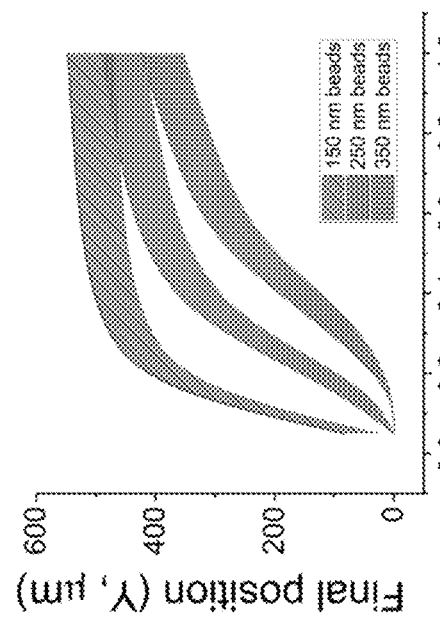
*FIG. 7C*

DEVICES, KITS, AND METHODS FOR LABEL-FREE FOCUSING AND/OR SEPARATION OF SUB-MICRON PARTICLES

CROSS-REFERENCE RELATED APPLICATION

This Application claims the benefit of U.S. Provisional Application entitled "DEVICES, KITS, AND METHODS FOR LABEL-FREE SEPARATION OF SUB-MICRON PARTICLES," having Ser. No. 62/874,941, filed on Jul. 16, 2019, which is incorporated herein by reference in its entirety.

STATEMENT REGARDING FEDERALLY SPONSORED RESEARCH OR DEVELOPMENT

This invention was made with government support under Grant Nos. 1659525, 1648035, 1150042 awarded by the National Science Foundation and Grant Nos. GM104528, UL1TR002378 awarded by the National Institutes of Health. The Government has certain rights in the invention.

BACKGROUND

Microfluidic particle and cell/biological particle sorting plays an important role in environmental monitoring, disease diagnostics, and therapeutics. Some techniques include labeling the particle or cell; however, these techniques have disadvantages. Thus, there is a need to develop alternative, label-free techniques for particle sorting. Moreover, there is a need for effective sorting and separation of sub-micron size particles and submicron biological entities in samples, such as biological samples.

Submicron sized particles and biological entities (10-1000 nm in diameter) have wide interests in both healthcare and industrial applications. For example, exosomes, a type of small extracellular vesicles with ~30-150 nm diameter secreted by their cells of origin and packed with lipids, proteins, RNA and DNA, are being studied for their role in cellular communication and its implication in clinical applications. The presence of exosome in bodily fluids, along with the information they carry, makes them attractive candidates for medical diagnostic and therapeutic tools. However, current technologies for manipulating submicron sized particle and biological entities, including high efficiency focusing and separation, are challenged with drawbacks including long processing time, high cost, and the need to use labeling agents for specific isolation.

SUMMARY

In accordance with the purpose(s) of the disclosure, as embodied and broadly described herein, the disclosure, in various aspects, relates microfluidic devices, kits including such devices, and methods of using microfluidic devices that overcome one or more of the aforementioned deficiencies. The devices and methods can combine filters, sheathing separation, and flow focusing to provide for high throughput focusing and separation of sub-micron particles.

Aspects of the present disclosure provide multi-stage microfluidic devices for enriching and/or sorting unlabeled, sub-micron size particles in a sample. Embodiments of mutli-stage microfluidic devices of the present disclosure include: a microfluidic channel having at least a first and second end; at least a first and second fluid inlet, at least a first and second stage, and at least a first and second outlet. Devices of the present disclosure include a first fluid inlet at the first end of the microfluidic channel and configured to receive a mixed sample fluid comprising the sample with the unlabeled, sub-micron size particles combined with a first ferrofluid, wherein the mixed sample fluid has a first flow rate. The devices further include a first stage after the first inlet comprising a filter region having one or more filters configured to separate a least a portion of larger microparticles or debris from the mixed sample fluid and a second fluid inlet after the filter region and configured to receive an optional sheathing ferrofluid at a second flow rate, wherein the first ferrofluid and the sheathing ferrofluid each comprise a plurality of magnetic nanoparticles, a surfactant and a carrier fluid. Devices of the present disclosure further include a second stage located after the second fluid inlet configured to flow components of the mixed sample fluid and the optional sheathing ferrofluid, the second stage comprising a magnetic source configured to produce a substantially symmetric magnetic field having a field minimum along an inner longitudinal axis of the microfluidic channel and sufficient to cause a the unlabeled sub-micron sized particles to be focused toward a center of the microfluidic channel of the second stage as a function of the size of the particles. The devices also include at least a first and second outlet at the second end of the microfluidic channel, wherein the first outlet is positioned to receive unlabeled sub-micron sized particles in fluid flowing along a center of the microfluidic channel and wherein the second outlet has at least one opening positioned to receive unlabeled sub-micron sized particles in fluid flowing along a periphery of the microfluidic channel. In embodiments of the devices of the present disclosure, the magnetic source comprises a first and second array of magnets, wherein the second stage is sandwiched between and substantially centrally aligned between the first magnet array and the second magnet array; and wherein the first magnet array and the second magnet array are in a quadrupole configuration and oriented to attract each other.

According to aspects of the present disclosure, the mutli-stage microfluidic devices of the present disclosure are configured to be operated in an enrichment mode or a sorting mode. In enrichment mode the device functions to hydrodynamically focus a heterogenous population of sub-micron sized particles in the mixed sample fluid toward the center of the microfluidic channel in the second stage and to the first outlet. In sorting mode, the sheathing ferrofluid is introduced at the second inlet and the sheath flow of the sheathing ferrofluid in combination with the substantially symmetric magnetic field functions to cause a first sub-population of the sub-micron sized particles to be focused toward a center of the microfluidic channel of the second stage to a greater degree than a second sub-population of the sub-micron sized particles having an average diameter smaller than the average diameter of the first population of sub-micron sized particles, such that a majority of the first sub-population of sub-micron particles flows to the first outlet and a majority of the second population of sub-micron particles flows to the second outlet.

The present disclosure also includes kits for enriching and/or sorting unlabeled, sub-micron size particles in a fluid sample, where the kits comprise a multi-stage microfluidic device of the present disclosure and a superparamagnetic composition comprising a plurality of magnetic nanoparticles and a surfactant. In embodiments, the superparamagnetic composition adapted to be combined with a carrier fluid to make a superparamagnetic fluid, wherein the superparamagnetic fluid can be the first ferrofluid, optional sheathing ferrofluid, or both for use in the multi-stage microfluidic device. Kits of the present disclosure can also comprise instructions for combining the magnetic nanoparticles, surfactant, and carrier fluid to make the superparamagnetic fluid.

Aspects of the present disclosure also provide methods of enriching and/or sorting unlabeled, sub-micron size particles in a sample comprising a plurality of components. In embodiments, the methods include introducing a mixed sample fluid comprising the sample with the unlabeled, sub-micron size particles and a first ferrofluid into the first fluid inlet of a multi-stage microfluidic device of the present disclosure. In embodiments, the method includes introducing the mixed sample fluid to the device at a first flow rate, filtering large debris and particles from the mixed sample fluid in the first stage of the device; and flowing the mixed sample fluid through the second stage of the device such that the substantially symmetric magnetic field produced by the magnetic force in the second stage hydrodynamically focuses the unlabeled sub-micron sized particles in the mixed sample fluid to move toward a center of the microfluidic channel of the second stage, such that the unlabeled sub-micron sized particles in fluid flowing along a center of the microfluidic channel flow toward a first outlet.

Embodiments of methods of the present disclosure also include introducing a sheathing ferrofluid into the second fluid inlet of the microfluidic device at a second flow rate, such that sheath flow of the sheathing fluid in combination with the substantially symmetric magnetic field functions to cause a first sub-population of the sub-micron sized particles in the mixed fluid sample to be focused toward a center of the microfluidic channel of the second stage to a greater degree than a second sub-population of the sub-micron sized particles having an average diameter smaller than the average diameter of the first population of sub-micron sized particles, such that a majority of the first sub-population of sub-micron particles flows to the first outlet and a majority of the second population of sub-micron particles flows to the second outlet.

Other systems, methods, devices, features, and advantages of the devices and methods will be or become apparent to one with skill in the art upon examination of the following drawings and detailed description. It is intended that all such additional systems, methods, devices, features, and advantages be included within this description, be within the scope of the present disclosure, and be protected by the accompanying claims

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A (left panel) is a schematic illustration of an extracellular vesicle (EV, 30-1000 nm in diameter) experiencing both diffusion and "particle ferrohydrodynamics" in a colloidally-stable magnetic nanoparticle (~10 nm particle diameter) suspension (i.e., ferrofluids). The magnetization of the unlabeled EV $M_{EV}$ is near zero and much less than its surrounding ferrofluids $M_{ferrofluid}$. The ferrohydrodynamic force on the EV is generated from magnetic nanoparticle-induced pressure imbalance on the vesicle's surface, which is proportional to the EV's volume. The intensity bar indicates the relative amplitude of the magnetic field strength. Arrows show the direction of vesicle movement, small black arrows on the EV's surface show the direction of magnetic nanoparticle-induced surface pressure. FIG. 1A (right panel) is a graph illustrating the relationship between characteristic migration time of a diamagnetic nanoparticle in ferrofluids and the diameter of the nanoparticle. The migration of nanoparticles is affected by both diffusion and "particle ferrohydrodynamics" and determined by the faster process out of the two. For nanoparticles with a diameter of less than ~30 nm, the diffusive process dominates the migration; for nanoparticles with a diameter of larger than ~30 nm, the ferrohydrodynamic process dominates the migration. FIG. 1B illustrates the working principle of an embodiment of a label-free continuous-flow EV focusing/separation device of the present disclosure, sometimes referred to herein as "FerroChip." In the focusing mode of device operation (top panel), samples of EVs were premixed with a dilute ferrofluid and entered a straight microchannel with a uniform distribution across the channel width. A symmetric magnetic field with its minimum in the middle of the microchannel was used to direct EVs towards the center of the microchannel, effectively focusing them into a narrow stream. The magnetic fields from a quadrupole array of permanent magnets, the flow velocity of the nanoparticles or EVs, together with the concentration of the ferrofluid, are chosen so that the diamagnetic nanoparticles or EVs will ferrohydrodynamically migrate towards the center of the microchannel regardless of their sizes, effectively focusing all of them into a narrow stream. In the sorting/separation mode (bottom panel), EVs entered the channel predominately through the regions close to the channel wall due to a sheath flow. The same magnetic field was used to direct unlabeled EVs from the sidewall region towards the channel center for continuous collection. The magnetic fields, and the flow velocity of the nanoparticles or EVs, together with the concentration of the ferrofluid, are chosen so that the ferrohydrodynamic migration of nanoparticles or EVs towards the center of the microchannel depends on their sizes. EVs of various sizes migrated towards the center of the microchannel, with varying speeds that depended on their sizes. Large EVs migrated to the channel center at a faster speed than smaller exosomes. Yellow arrows with gradients indicate the distribution of magnetic fields in the microchannel. FIG. 1C illustrates a top-view schematic drawing of the FerroChip's microchannel. Initial samples of nanoparticles and/or EVs were injected into the channel from inlet 1. The samples, after first going through a debris filter that removed large debris, entered a straight channel (labeled as focusing/separation region) which focused or separated nanoparticles and/or EVs based on their sizes. Processed samples were collected from middle and side outlets for characterizations. In embodiments, when the FerroChip operates in focusing mode, inlet 2 (sheath flow) is not used. When the FerroChip operates in separation mode, inlet 2 provides a ferrofluid sheath flow so that nanoparticles and/or EVs entered from the top and bottom walls of the channel. The width, height and length of the microchannel are 1200 µm, 150 µm and 53 mm, respectively. FIG. 1D shows digital images of a microchannel (left, blue ink indicating the channel geometry) and assembled FerroChip with four permanent magnets in quadrupole configuration inside a holder (right). The microfluidic device and permanent magnets were placed within an aluminum manifold during its operation. Scale bars: 1 cm.

FIG. 2A illustrates optimization of high magnetic flux densities and high magnetic flux density gradients in the FerroChip for nanoparticle focusing. Using four permanent magnets (38.1 mm by 6.35 mm by 6.35 mm, N52 neodymium magnet) in a quadrupole configuration shown here in the center, a magnetic flux density of up to 0.5 T in the x-y plane (z=0), and a magnetic flux density gradient of 1272 T m$^{-1}$ in the y-z plane (x=0) were obtained. Under the magnetic field of the quadrupole magnets, simulation of submicron particle trajectories for 520 nm polystyrene beads in ferrofluids in x-y plane (left-bottom), x-z plane (left top), and y-z plane (right), were conducted to study the effectiveness of FerroChip in focusing 520 nm diamagnetic beads. A sample inlet flow rate of 3 µL min$^{-1}$ and a ferrofluid concentration of 0.3% (v/v) were used in the simulation. Results show that 520 nm beads could be focused in all three dimensions in the prototype device. Triangles in the trajectory plots indicate the starting points of particles. FIG. 2B (Left panel) provides experimental bright-field images showing that 520 nm diamagnetic polystyrene beads inside a microchannel can be focused into a narrow stream in the presence of the ferrofluid and quadrupole magnets, using optimized parameters from FIG. 2A. FIG. 2B (Right panel) provides experimental fluorescence images that confirm the focusing effects on 520 nm polystyrene. A sample inlet flow rate of 3 µL min$^{-1}$ and a ferrofluid concentration of 0.3% (v/v) were used in FIG. 2B. Scale bar: 200 µm.

FIG. 3A shows optimizations of nanoparticles focusing with parameters including nanoparticle diameters and flow rates through both simulations and experiments. Simulation results agreed with experimental results reasonably well. Both confirmed that the ferrohydrodynamic focusing effect on nanoparticles depended on the diameters of particles in ferrofluids. As the particle size increased, the focusing effect became more pronounced. Additionally, as the flow rates in the microchannel increased, the focusing effect decreased. Particle stream width of the y-axis label indicates the width of the focused particle stream. Gray shaded area indicates the width of the collection outlet in the FerroChip. A panel of fluorescent images (right) captured during the focusing of 100 nm, 380 nm, 520 nm, and 1000 nm polystyrene beads at a flow rate of 5 µL min$^{-1}$ illustrates that focusing effect depended on particle sizes. FIG. 3B illustrates optimizations of nanoparticles focusing with the parameter of ferrofluid concentration through both simulations and experiments. Simulation results agreed with experimental results reasonably well. Both confirm that the ferrohydrodynamic focusing effect on submicron beads depended on the ferrofluid concentration. As the ferrofluid concentration increased, the focusing effect became more pronounced. A panel of fluorescent images (bottom) captured during the focusing of 520 nm polystyrene beads at 0.05%, 0.1%, 0.2% and 0.3% (v/v) ferrofluid concentration illustrates that focusing effect depended on ferrofluid concentrations. Flow rate was 5 µL min$^{-1}$. Scale bar is 200 µm in all images.

FIG. 4A is a panel of images showing simulation results of the separation of 200 nm and 1000 nm polystyrene beads, at different flow rates (1-10 µL min$^{-1}$) in a 0.3% (v/v) ferrofluid. 1-3 µL min$^{-1}$ were selected as—flow rates because they correspond to more than 400 µm separation distance in simulation. A 3 µL min$^{-1}$ optimal flow rate was chosen to separate 200 nm and 1000 nm polystyrene beads from each other. The ratio of particle flow and sheath flow was 1:5 (sample—3 µL min$^{-1}$; sheath—15 µL min$^{-1}$). Other simulation parameters included a ferrofluid concentration of 0.3%, and the same quadrupole magnet configuration in previous figures. Using these parameters, the distribution of 200 nm and 1000 nm beads was simulated at the outlets of the FerroChip. Particle trajectories from the simulation results predicted that the two differently sized particles could be completely separated. FIG. 4B illustrates the experimental device design and viewing windows and experimental images of the separation of a mixture of 200 nm (blue) and 1000 nm (red) polystyrene particles in the FerroChip. Fluorescent images taken at different locations along the microchannel showed that 200 nm particles (blue) were completely separated from 1000 nm particles (red). Both particles were collected for subsequent size characterization. Broad blue fluorescent signals across the channel at the location #3 were from the shade of the permanent magnets, not fluorescent particles. FIG. 4C is a series of graphs of particle size distributions measured by Dynamic Light Scattering (DLS) indicating a well-separated 1000 nm and 200 nm particles after FerroChip processing.

FIG. 5A illustrates the device design and flow rates; a 1 µL min$^{-1}$ sample flow rate was chosen in order to separate exosome-like nanoparticles (30-150 nm in diameter) from extracellular media and human serum. This sample flow rate maximized the separation between exosome-like nanoparticles and large EVs (200-1000 nm in diameter). The ratio of sample flow and sheath flow was 1:5 (sample—1 µL min$^{-1}$; sheath—5 µL min$^{-1}$). Other device and operating parameters remained the same as in previous figures. FIG. 5B provide super-resolution microscopic images of exosome-like nanoparticles (PKH 67 green fluorescence) and large EVs (PKH 26 red fluorescence) from the mixture (pre-separation), and the samples after FerroChip processing (large EVs and exosome outlets). A total of 730 particles were analyzed. FIG. 5C is an image of Western blot analysis of CD63 and HSP70 protein levels in large EVs and exosome-like nanoparticles that were processed by the FerroChip. FIG. 5D provides transmission electron microscopy (TEM) images of exosome-like nanoparticles collected from the FerroChip. FIG. 5E is a graph of size distribution of separated exosome-like nanoparticles from TEM images (n=755). FIG. 5F illustrates immunofluorescence images of separated exosome-like nanoparticles from human serum. Three channels were used in immunofluorescent staining, including EpCAM (green), CD24 (red), and CD63 (cyan). FIG. 5G is a Venn diagram depicting the percentage of antibody presence on the surfaces of separated exosome-like nanoparticles (n=12000) from human serum. EpCAM+alone: 5%; CD24+ alone: 52%; CD63+ alone: 21%; EpCAM+ and CD24+:4%; EpCAM+/CD63+:2%; CD24+/CD63+:14%; CD63+/CD24+/EpCAM+:2%.

FIGS. 7A-7C are a series of graphs illustrating the theoretical size resolution of the FerroChip and its potential in fractionation of a heterogeneous extracellular vesicles (EV) sample. The simulation uses the same device geometry, ferrofluid concentration/composition and magnetic fields of the FerroChip reported in this study. Variable parameters in this simulation include the sample flow rate and particle sizes. FIG. 7A Simulation results of binary particles separation with a diameter difference of 100 nm at variable sample flow rates. Y-axis is the separation distance between the two particle streams. The dashed line of 100 µm on the Y-axis is the minimal separation distance with which binary particles are considered to be separated. FIG. 7B illustrates simulation results of fractionation of a heterogeneous EV sample in the FerroChip at variable flow rates. Y-axis is the end of separation region in the FerroChip. Bands of EVs with 100 nm diameter range are labeled. FIG. 7C shows simulation results of fractionation of a sample with three different sized beads in the FerroChip at variable flow rates. Y-axis is the end of separation region in the FerroChip.

DETAILED DESCRIPTION

Figure 1A:
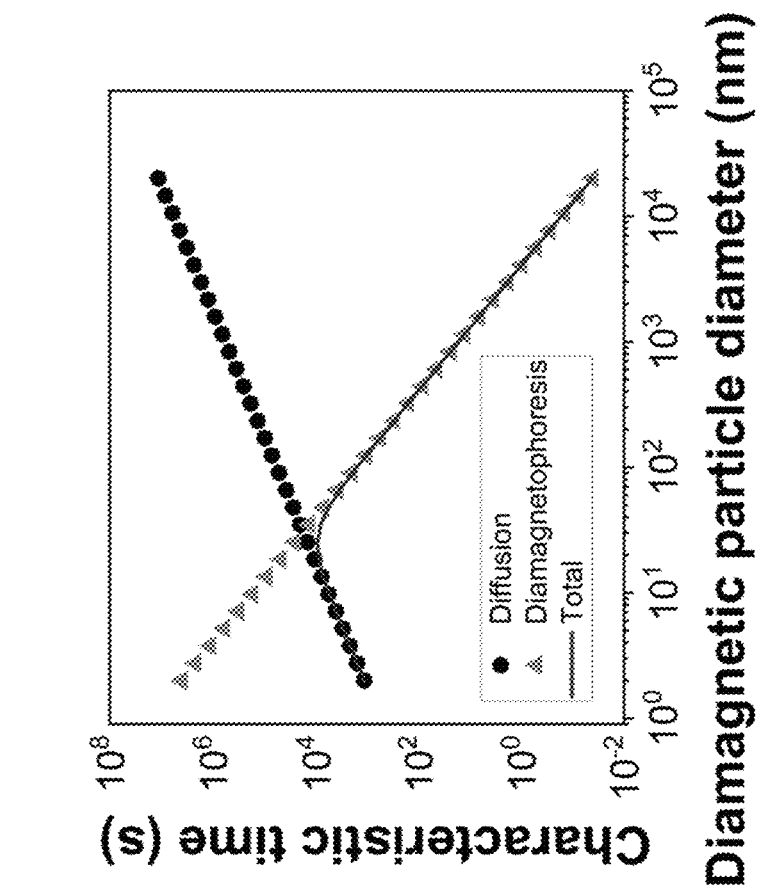
FIGS. 1A-1D illustrate various aspects and operating principles of a label-free ferrohydrodynamic nanoparticle separation device according to the present disclosure.
Figure 1A:
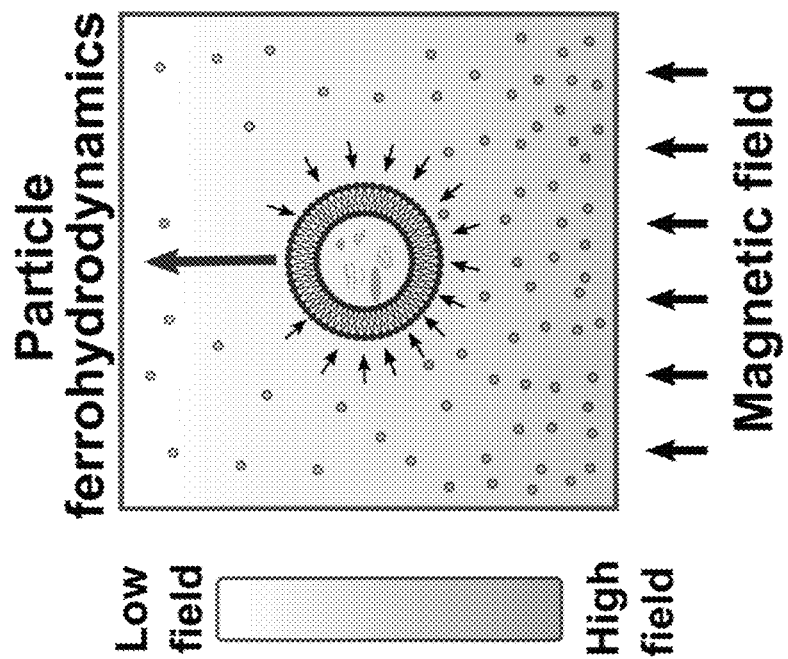

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, biology, molecular biology, microfluidics, and the like, which are within the skill of the art. Such techniques are explained fully in the literature.

The following examples are put forth to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20-25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

All publications and patents cited in this specification are cited to disclose and describe the methods and/or materials in connection with which the publications are cited. Publications and patents that are incorporated by reference, where noted, are incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. Any terms not specifically defined within the instant application, including terms of art, are interpreted as would be understood by one of ordinary skill in the relevant art; thus, is not intended for any such terms to be defined by a lexicographical definition in any cited art, whether or not incorporated by reference herein, including but not limited to, published patents and patent applications. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Prior to describing the various embodiments, the following definitions are provided and should be used unless otherwise indicated.

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" indicates that the subsequently described event or circumstance can or cannot occur, and that the description includes instances where said event or circumstance occurs and instances where it does not.

As used herein, "kit" refers to a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" refers to documents describing relevant materials or methodologies pertaining to a kit. These materials may include any combination of the following: background information, list of components and their availability information (purchase information, etc.), brief or detailed protocols for using the kit, troubleshooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents and are meant to include future updates.

As used herein, "sub-micron" refers to a size less than about 1 μm, such as particles in the nanometer range. In embodiments sub-micron particles of the present disclosure have a diameter of about 10 to about 1000 μm, about 100 to about 1000 μm, about 200 to about 800 μm, and so forth.

As used herein, the term "biocompatible," with respect to a substance or fluid described herein, indicates that the substance or fluid does not adversely affect the short-term viability or long-term proliferation of a target biological particle within a particular time range.

"Curved" or "curve," as described herein, indicates a non-linear shape, where curved can include a single curve, multiple curves, and multi-directional curves, including crescent-shaped, serpentine, and the like.

Discussion

In accordance with the purpose(s) of the present disclosure, as embodied and broadly described herein, embodiments of the present disclosure, in some aspects, relate to devices, kits, and methods for focusing/enriching and/or separating/sorting particles, specifically submicron particles and biological entities and the like. Devices, kits, and methods of the present disclosure utilize ferrohydrodynamic manipulation to focus populations of submicron particles into a stream for enrichment as well as to optionally further separate submicron size particles from other particles in a sample (e.g., a biological sample) based on the size (e.g., volume) of the particles and/or to further sort various subpopulations of submicron particles based on size differences. Embodiments of such devices, kits and methods facilitate separation of exosomes (submicron size extracellular vesicles) from biological samples.

Current technologies for manipulating submicron sized particles and sub-micron sized biological entities (e.g., exosomes), face drawbacks such as long processing time, high cost, and the need to use labeling agents for specific isolation of the sub-micron particles. However, these small particles have large value and interest in healthcare and industrial fields. For example, exosomes—small, extracellular vesicles having average diameters of about ~30-150 nm diameter secreted by cells and containing lipids, proteins, RNA and DNA—are currently a major focus of study for their role in cellular communication and its implication in clinical applications. Exosomes are present in bodily fluids (e.g., blood, extracellular fluid, etc.), but an efficient method of focusing and separating them from these fluid samples is needed so they can be used in research, such as for medical diagnostic and therapeutic tools.

The present disclosure describes devices, kits, and methods that employ a label-free ferrohydrodynamic manipulation scheme that is capable of focusing and separating/sorting submicron particles and biological entities based on their volumes. The approach is based on "diamagnetophoresis" of submicron sized particles and biological entities in a colloidal magnetic nanoparticle suspension (ferrofluids). This approach has been used with micron sized particles and cells but has not been effectively used to manipulate and separate smaller submicron sized particles, which have different properties and behaviors than the larger micron-sized particles.

In various aspects, microfluidic devices and methods of using microfluidic devices are provided for high throughput focusing, separation, and/or manipulation of sub-micron sized particles in a sample, including, but not limited to a biological sample such as, but not limited to, blood, plasma, urine, and other biological fluids. In some aspects, the devices are single-stage devices, while in some aspects the devices have multiple stages. Therefore, the terms first, second, third and so-on, when used to describe the stages, should not be considered limiting on the total number of stages but is used for simplicity to describe the relative ordering of the stages. Additional stages, not explicitly described, may in some aspects appear before the first stage. In some embodiments, devices and kits of the present disclosure may include multiple stages, such as, but not limited to a filter stage, a focusing/enrichment stage, and sorting/separation stage.

Embodiments of the present disclosure are advantageous because of the ability to focus/enrich/separate sub-micron particles from a sample at a very high recovery rate (e.g., about 95% or more, about 97% or more (+/− about 2.3%), about 99% or more, etc.) and a high purity (e.g., 87% or more, about 80% or more, about 95% or more (+/− about 4.1%, etc.) at throughputs of up to about 1-20 μL/min. In addition, the device is less expensive and less time-consuming than other techniques and is straightforward to operate. Embodiments of the present disclosure are also advantageous in that, for biological samples and biological sub-micron particles, neither short-term nor long-term viability are impacted.

The devices, kits, and methods of the present disclosure use magnetic fields to focus/enrich sub-micron particles in a sample and/or sort/separate the sub-micron particles based on the size/volume of the particles. Under magnetic fields, particles, including sub-micron size particles (e.g., nano-size particles including, but not limited to, sub-cellular particles, such as exosomes) can experience the generated magnetic field direction to produce a magnetic buoyancy force, analogous to buoyancy force, as magnitude of the force is proportional to the volume of cell. This force can be used to spatially separate cells of different sizes in certain flow conditions (e.g., laminar flow and/or shear flow).

Embodiments of the present disclosure can be label-free and/or do not require time-consuming conjugations steps (e.g., to magnetic beads, targeting moieties, fluorescent labels, etc.). Although some systems claim to be label-free, embodiments of the present disclosure can be truly label-free in that the target sub-micron particles do not need a label for separation, but are separated based on volume/size alone, without being conjugated to a label.

Embodiments of the present disclosure include high-efficiency and high-throughput continuous-flow sup-micron particle enrichment/separation systems/kits and devices using magnetic fluid (e.g., ferrofluids, such as superparamagnetic sheathing fluids) and magnets (e.g., permanent magnets). Permanent magnet-based devices are low-cost, easy to operate, and their operation does not generate heat. Magnetic fields produced by permanent magnets are substantially larger than the ones by current-carrying electrodes, and this larger field can increase the sorting throughput and efficiency of embodiments of the present disclosure. Embodiments of the present disclosure provide for devices and systems that can easily fit onto a normal glass microscope slide for ease of observation under the microscope.

Now that the devices, systems/kits, and methods have been described generally, exemplary embodiments are described below. Embodiments of multi-stage microfluidic devices of the present disclosure can be used for focusing and enriching unlabeled, sub-micron size particles in a sample and/or for sorting/separating sub-populations of unlabeled, sub-micron size particles based on size of the particles. In Embodiments, devices for enriching and/or sorting unlabeled, sub-micron size particles in a fluid sample include a microfluidic channel, with at least two inlets, a filter stage, a focusing/separation stage including a magnetic source, and at least two outlets.

According to aspects of the disclosure, the microfluidic channel of the device has first and second end. The device can further include a first fluid inlet at the first end of the microfluidic channel and configured to receive a fluid sample including the sub-micron size particles. The fluid sample introduced at the first inlet includes a sample including sub-micron particles. The sample can be a fluid and can be prepared from particles and carrier fluids or can be obtained, such as a sample from a host (e.g., blood, extracellular fluid, urine, other biological fluids, etc.). In some embodiments, a sample from a host has be pre-treated or processed to removed larger cells, agglomerates, and other biological debris. For instance, if the sample is whole blood, it would be processed first (e.g., by centrifugation) to separate blood cells and other circulating cells or other bodies from plasma and smaller (e.g., sub-micron sized) particles such as exosomes. This sample is then combined with a first ferrofluid to make a mixed sample fluid comprising the sample with the unlabeled, sub-micron size particles and the first ferrofluid. The mixed sample fluid has a first flow rate upon introduction to the first inlet.

Devices of the present disclosure also include a first stage after the first inlet where the first stage includes a filter region having one or more filters configured to separate large particles (e.g. larger micron-sized particles) and debris (some of which could be left over from device fabrication) from the sample. In embodiments, the filters separate/remove particles larger than about 30 μm from the sample. In some embodiments, the device can include a curve located after the filter region which can conserve space and can also function to focus the flow of particles as they enter the second stage.

The multi-stage micro-fluidic devices of the present disclosure, according to various aspects, also include a second fluid inlet after the filter region (in embodiments with a curve after the filter region, the second fluid inlet is located after curve). The second fluid inlet is configured to receive an optional sheathing ferrofluid (which can also be referred to as a superparamagnetic sheathing fluid) at a second flow rate. Each of the first ferrofluid and the sheathing ferrofluid include a plurality of magnetic nanoparticles, a surfactant, and a carrier fluid. In embodiments (e.g., where the sample is a biological sample) the ferrofluid is a biocompatible ferrofluid including a biocompatible surfactant and biocompatible carrier fluid). In embodiments, the magnetic nanoparticles in the ferrofluid have an average diameter of about 8-12 nm (including intervening ranges, such as, but not limited to, about 8-11 nm, about 9-12 nm, about 10-11 nm, etc.). As described in more detail below, in embodiments, the superparamagnetic fluid can have a concentration of magnetic nanoparticles of about 0.3% to 1% (v/v) prior to mixing with sample or dilution as sheathing fluid. In embodiments this superparamagnetic fluid can be the first ferrofluid that is combined with the sample prior to or at the first inlet, to make the mixed sample fluid. In embodiments, when the first ferrofluid is mixed with the sample, the mixed sample fluid has a concentration of magnetic particles of about 0.01 to 0.6% (v/v), such as about 0.05-0.3%. In some embodiments the volume concentration of magnetic nanoparticles of the optional sheathing ferrofluid (introduced at the second inlet) is between about 50% and 90% of the volume concentration of magnetic nanoparticles in the mixed sample fluid. The sheathing ferrofluid is described herein as optional because the sheathing fluid is added depending on the mode of operation of the device, as described in greater detail in the description of the methods below. Briefly, if operating in enrichment mode, with the goal of enriching the amount of sub-micron particles (e.g., a heterogeneous population of sub-micron particles of various sizes) in a sample, then the sheathing ferrofluid is not typically used. If the goal is to sort/separate different sub-populations of sub-micron size particles based on size, then the sheathing ferrofluid is added at the second inlet to generate sheath flow which aids in further size separation, as described below.

Devices of the present disclosure also include a second stage located after the second fluid inlet configured to flow the components of the mixed sample fluid and the optional sheathing ferrofluid into a stream by sheath flow. The second stage includes a magnetic source configured to produce a substantially symmetric magnetic field having a field minimum along an inner longitudinal axis of the microfluidic channel. The magnetic field in the second stage is sufficient to cause a cause the unlabeled sub-micron sized particles to be focused toward a center of the microfluidic channel of the second stage. The sub-micron size particles are focused as a function of size of the particles, but without sheath flow, the particles generally all migrate toward the center of the microfluidic channel to form a focused stream of particles flowing along a center (e.g., near the longitudinal diameter) of the microfluidic channel and away from a periphery of the channel (e.g., towards the outer edge of the channel) as illustrated in the top panel of FIG. 1B. Finally, devices of the present disclosure include at least a first and second outlet, where the first outlet is positioned to receive the unlabeled sub-micron sized particles in fluid flowing along a center of the microfluidic channel. The second outlet has at least one opening positioned to receive a any unlabeled sub-micron sized particles and/or other materials and fluid flowing along a periphery of the microfluidic channel.

As described above, the device is configured to be operated in an enrichment mode or a sorting mode. In enrichment mode, as described above and illustrated in FIG. 1B (top), the device functions to hydrodynamically focus a heterogenous population of sub-micron sized particles in the mixed sample fluid toward the center of the microfluidic channel in the second stage and to the first outlet. In sorting/separation mode, the sheathing ferrofluid is introduced at the second inlet and the sheath flow of the sheathing ferrofluid in combination with the substantially symmetric magnetic field functions to cause a first sub-population of the sub-micron sized particles to be focused toward a center of the microfluidic channel of the second stage to a greater degree than a second sub-population of the sub-micron sized particles having an average diameter smaller than the average diameter of the first population of sub-micron sized particles, such that a majority of the first sub-population of sub-micron particles flows to the first outlet and a majority of the second population of sub-micron particles flows to the second outlet. It is also contemplated that embodiments of devices of the present disclosure could include additional stages (e.g., a third stage, fourth stage, etc.) such that the device could conduct both enriching and sorting simultaneously. For instance, a device of the present disclosure could include a first stage as described above and a second stage as described above (with or without the second inlet) adapted for operation in enriching mode, and then a third stage with features the same or similar to the second stage as described above (e.g., with an inlet—e.g., a second inlet or a third inlet for introduction of a sheeting fluid, and a magnetic source) adapted for operation in sorting mode. In embodiments, there could be intermediate outlets and/or collection reservoirs between the second stage and third stage to collect an enriched sample prior to introduction into a third stage for sorting.

Illustrative embodiments of the device are shown in the figures below. The components (e.g., particles) of the mixed sample fluid and sheathing ferrofluid are focused and/or separated as a function of component size (e.g. the diameter of particles, volume of the particle) and width of the microfluidic channel and magnetic buoyancy force on the particles generated by the magnetic field applied to the channel. For clarity, the microfluidic channel may be described as a curved microfluidic channel, but it should be understood that the channel may have various shapes or paths, including but not limited to straight, one or more angles or curves (e.g. polygonal, having one or more right, acute and/or obtuse angles), serpentine, and the like.

In an embodiment, the sample fluid can include a plurality of components, both sub-micron size, micron size and larger. In embodiments, the larger particles are removed by the filters in the first stage. The sample fluid can be a biological sample (e.g., blood) including various biological components, such as cells, and sub-cellular particles, such as exosomes, macro-molecules, etc. In an embodiment, sub-cellular, sub-micron sized particles that have size difference can be distinguished by this technique. In an embodiment, the sample fluid is a biological fluid in which cells have been lysed to release sub-cellular particles. In embodiments, the sample fluid is a biological fluid and some of the sub-micron sized particles are exosomes, which typically have a size in the range of about 30-150 nm. In embodiments the device of the present disclosure can be used to focus and separate exosomes from other extracellular vesicles having sub-micron sizes, such as microvesicles, having a diameter in the range of 100-1000 nm. The sample fluid can also be a non-biological sample including other types of sub-micron sized particles. As explained above, with the devices, kits, and methods of the present disclosure, the sub-micron target particles are separated without the need for labeling the particles. Thus, in embodiments, the particles are unlabeled.

In an embodiment, the components of the fluid sample can experience magnetic force and are compatible with the first ferrofluid and sheathing ferrofluid. In particular, the components can be separated by the magnetic buoyancy force exerted upon them. In an embodiment, the fluid is exposed to a magnetic force (e.g., a substantially symmetric magnetic force) generated by a magnetic device (e.g., an array of permanent magnets). In an embodiment, the components experience a magnetic buoyancy force that causes the components to focus to an area of the channel and separate from one another based on the volume of the components.

In an embodiment, the magnetic fluid can be a ferrofluid including magnetic particles, wherein the ferrofluid concentration is tunable from about 0.01% to 0.6% volume fraction of the magnetic particles in the ferrofluid. The concentration is tuned based on the size and volume fraction of the components of the magnetic particles. In an embodiment, the ferrofluid concentration is tunable from about 0.01% to 0.6%, such as about 0.05% to 0.3%, volume fraction of the magnetic particles in the ferrofluid. In an embodiment, the magnetic fluid can be a ferrofluid, paramagnetic solution, or a combination thereof. In an embodiment, the magnetic fluid can be a colloidal mixture of nano-size magnetic particles (e.g., about 5 to 20 nm in diameter, such as an average diameter of about 8-12 nm), covered by a surfactant, suspended in a compatible carrier medium. The magnetic particles can be iron oxide particles, cobalt particles, cobalt ferrite particles, iron particles, FePt particles, or a combination thereof, where the amount of the magnetic particles in the magnetic fluid can be about 0.025% (v/v) to 0.3% (v/v), such as about 0.05-0.3% (v/v), about 0.025-0.27% (v/v), and the like. The surfactant can include an electric double layer surfactant, polymer surfactant, inorganic surfactant, or a combination thereof. The carrier medium can be water, hydrocarbon oil, kerosene, or a combination thereof. In an embodiment, the magnetic fluid can include maghemite nanoparticles, a polymer surfactant, and the carrier can be water. In an embodiment, the magnetic fluid can include maghemite nanoparticles ($Fe_2O_3$) coated with polymethyl methacrylate-polyethylene glycol (PMMA-PEG) and 10% (v/v) 10× Hank's balanced salt solution (HBSS).

In some embodiments a stock ferrofluid solution can be used. In embodiments, a stock solution with a concentration of 0.3% can be used. It can also be diluted with PBS or other compatible fluid if needed. In embodiments of the device, kits and methods of the present disclosure, ferrofluid is mixed with both the sample to form the mixed sample fluid and used as sheathing ferrofluid. In embodiments, the sample fluid is pre-mixed with ferrofluid prior to introduction into the first inlet to produce the mixed sample fluid. In some examples, the mixed sample fluid has a concentration of magnetic nanoparticles of about 0.01 to 0.6% (v/v), such as, but not limited to, about 0.5 to 0.3% (v/v). In some embodiments, this mixed sample fluid is introduced in the first fluid inlet and then the optional sheathing ferrofluid can be introduced in the second inlet. In some such embodiments, the concentration of magnetic nanoparticles of the sheathing ferrofluid is less than about 90% of the mixed sample fluid concentration. In embodiments the concentration of the sheathing ferrofluid is between about 50% and 90% of the concentration of the mixed sample fluid. For example, if the mixed sample fluid has a concentration of about 0.3%, then the sheathing ferrofluid can have a concentration of magnetic nanoparticles of less than or equal to about 0.27%.

In embodiments, the fluid sample is a biological fluid and thus the superparamagnetic fluid should be biocompatible to maintain the viability and integrity of the components. Thus, in embodiments, a biocompatible superparamagnetic fluid (also referred to herein as a "ferrofluid") of the present disclosure is a colloidal suspension of magnetic nanoparticles, coated by a biocompatible surfactant and suspended in a carrier fluid. The ferrofluid of such embodiments is biocompatible and non-toxic to CTCs. In embodiments, the magnetic nanoparticles are a non-toxic magnetic material, such as, but not limited to iron oxide materials (e.g., magnetite ($Fe_3O_4$), maghemite ($Fe_2O_3$), and combinations of these. In embodiments, the magnetic nanoparticles are iron oxide particles (e.g., maghemite ($Fe_2O_3$)). Materials such as iron, cobalt, cobalt ferrite, and FePt are potentially toxic to cells, but could potentially be used if first rendered biocompatible/nontoxic by biocompatible coatings, etc. The magnetic nanoparticles can have a diameter of about 1-20 nm. In embodiments they have an average diameter of about 8-12 nm (e.g., about 10-11 nm). In embodiments, the magnetic nanoparticles are coated in a biocompatible surfactant to reduce agglomeration and to increase biocompatibility. In embodiments, the biocompatible surfactant can include electric double layer surfactant, polymer surfactant, inorganic surfactant, or a combination thereof. In embodiments, the surfactant is polymethyl methacrylate-polyethylene glycol (PMMA-PEG). In embodiments, the carrier medium can include biocompatible carrier fluids, such as, but not limited to, water, salt solution, or a combination. In embodiments, the carrier medium is a balanced salt solution, such as Hank's balanced salt solution (HBSS). In an embodiment, the biocompatible superparamagnetic fluid includes maghemite nanoparticles ($Fe_2O_3$) coated with polymethyl methacrylate-polyethylene glycol (PMMA-PEG) and 10% (v/v) 10× Hank's balanced salt solution (HBSS). In embodiments, the pH is about 7, and the osmotic pressure is close to that of a biological (e.g., human) cell. In embodiments, the ferrofluid concentration (volume fraction of magnetic particles) is as described above. The viscosity of the biocompatible superparamagnetic fluid varies based on the concentration of magnetic particles, the surfactant chosen, as well as the carrier fluid. In embodiments, the viscosity of the ferrofluid is about 0.95 mPa·s to 1.1 mPa·s. In embodiments the concentration of magnetic nanoparticles in the superparamagnetic fluid (after combination with carrier but before combination with sample to make a mixed sample fluid or before dilution to make a sheathing ferrofluid) is about 0.3% to 1% (v/v), and concentrations of the mixed sample fluid and optional sheathing fluid are described above.

In embodiments the magnetic source in the microfluidic devices include a first and second array of magnets (e.g., permanent magnets). In embodiments, the second stage is sandwiched between and substantially centrally aligned between the first magnet array and the second magnet array, which, in embodiments, are arranged such that the first magnet array and the second magnet array are in a quadrupole configuration and oriented to attract each other (e.g., opposite poles facing each other). This arrangement is configured to produce a magnetic field having the filed minimum along a central portion of the channel (e.g., an inner/substantially central longitudinal axis of the channel). This differs from the configuration used for separation of microparticles, which can be set up to have magnet arrays oriented to repel each other with a field maximum along a central portion of the channel. However, that configuration is not as effective for submicron sized particles because the magnetic flux density for repelling magnets is smaller than that of attracting magnets (with repelling magnets, the magnetic flux density is zero or near zero at the center, so the magnetic buoyancy force on the nanoparticles is so small they will not be easily moved/focused.

In embodiments, the magnetic source is configured to produce a magnetic field flux density up to about 0.5T, e.g. a magnetic field flux density that ranges from about 0 to about 0.5T, within the microfluidic channel, wherein the magnetic field flux density is lower (e.g., can be about 0 T) near a central longitudinal axis of the channel and higher (e.g., up to about 0.5T) near outer portions of the channel. In embodiments, the magnetic source is configured to produce a magnetic field flux density gradient within the channel of about 820 to 1272 T m$^{-1}$.

Although the microfluidic device can have various sizes and geometries, certain parameters were determined to aid separation of such small particles. In embodiments, the microchannel of the microfluidic device has a depth/thickness/height of about 50-500 µm and a width of about 300-1200 µm. In embodiments, the length of the second stage (e.g., focusing stage) is about 45-57 mm. As described above, in some embodiments, the device has a curve after the filter section and before the second inlet. In embodiments, the curve has an angle of curvature of about 120° to about 300°. In embodiments, the device may have additional curves and may be serpentine. In embodiments, the "curve" could include two 90° turns (e.g., a more "squared" curve)

In focusing mode, a heterogeneous population of sub-micron particles (e.g., mixture of various size sub-micron particles) are focused toward the center and generally toward the first outlet. In embodiments, a majority of the sub-micron particles in the sample are focused to the first outlet. Embodiments of the devices of the present disclosure can also include one or more collection chambers coupled to each of the first and second outlet for collecting particles from the respective outlets. Thus, in focusing mode, a majority of the sub-micron particles in the sample can be collected in a collection chamber coupled to the first outlet. In embodiments where the device is operated in sorting/separation mode, the first sub-population of unlabeled sub-micron sized particles has a larger average diameter than the second population of unlabeled sub-micron sized particles, such that the first population is focused toward the center of the channel in the second stage and toward the first outlet to a greater degree than the second sub-population. The second sub-population of particles, having an average diameter smaller than the average diameter of the first sub-population of particles experiences a lesser force and is thus only slightly focused to the middle of the channel. As a result, the second sub-population of smaller particles flows more on the outer portion (e.g., towards a periphery) of the channel towards a second outlet (and/or additional outlets). Thus, a majority of the first sub-population of sub-micron particles flows to the first outlet and a majority of the second population of sub-micron particles flows to the second outlet. In embodiments, the device also includes a separate collection chamber coupled to each of the first and second outlet for collecting the first and second sub-population of particles, respectively.

Embodiments of the present disclosure, as briefly mentioned above, also include kits including a multi-stage microfluidic device of the present disclosure described above and a superparamagnetic composition including a plurality of magnetic nanoparticles and a surfactant. The superparamagnetic composition can be combined with a carrier fluid to make a superparamagnetic fluid (ferrofluid), wherein the superparamagnetic fluid can be the first ferrofluid, the optional sheathing ferrofluid, or both, for use in the multi-stage microfluidic devices and kits of the present disclosure. In embodiments, the kit includes the microfluidic device and a superparamagnetic composition including a plurality of magnetic nanoparticles and a surfactant, the superparamagnetic composition adapted to be combined with a carrier fluid to make a ferrofluid to be used as the first ferrofluid and/or sheathing ferrofluid (as described above) and instructions for making the ferrofluid. In embodiments, the kit includes the microfluidic device, the magnetic nanoparticles, the surfactant, and optionally a carrier fluid, and further includes instructions for combining the magnetic nanoparticles, surfactant, and carrier fluid to make the ferrofluid. In embodiments, the ferrofluid can have a concentration as described above and magnetic nanoparticles having sizes as described above. In embodiments if the kit is to be used with biological samples, the superparamagnetic composition and carrier can be biocompatible and include instructions for preparing a biocompatible ferrofluid, as described above.

In embodiments of systems or kits of the present disclosure, the kit/system may include the fully prepared superparamagnetic fluid, also referred to herein as a "ferrofluid", as described above, and/or a prepared superparamagnetic composition (also sometimes referred to as ferromagnetic composition even though the composition/fluid does not technically become magnetic until in the presence of a magnetic field) along with instructions for diluting the superparamagnetic composition or ferrofluid with additional carrier fluid to adjust the concentration/volume fraction of magnetic nanoparticles in the first ferrofluid, the mixed sample fluid and/or sheathing ferrofluid. In embodiments, systems or kits of the present disclosure may include a biocompatible superparamagnetic composition that includes the plurality of magnetic nanoparticles and instructions for combining the magnetic nanoparticles with a biocompatible surfactant (if not already combined with surfactant) and biocompatible carrier fluid to make a biocompatible superparamagnetic fluid of the present disclosure. In embodiments, systems/kits of the present disclosure can include the plurality of magnetic nanoparticles and the surfactant (separately or mixed (e.g., such that the surfactant coats the magnetic nanoparticles) and instructions for combining the superparamagnetic composition with a carrier fluid to make a superparamagnetic fluid of the present disclosure.

Embodiments of the present disclosure also include methods of focusing/enriching unlabeled, sub-micron size particles in a fluid sample comprising a plurality of components by using the multi-stage microfluidic devices described above. Methods of the present disclosure can also include sorting/separating sub-populations of sub-micron size particles in a fluid sample. In embodiments, such methods can include introducing a mixed sample fluid comprising the sample with the unlabeled, sub-micron size particles and a first ferrofluid into the first fluid inlet of a multi-stage microfluidic device of the present disclosure at a first flow rate and filtering large debris and particles from the mixed sample fluid in the first stage of the device. Then the mixed sample fluid flows through the second stage of the device such that the substantially symmetric magnetic field produced by the magnetic force in the second stage hydrodynamically focuses the unlabeled sub-micron sized particles in the mixed sample fluid to move toward a center of the microfluidic channel of the second stage, such that the unlabeled sub-micron sized particles in fluid flowing along a center of the microfluidic channel flow toward a first outlet. Depending on the addition or not of the optional sheathing ferrofluid and the flow of the mixed fluid sample in the device, the particles can be either enriched or sorted.

Figure 1B:
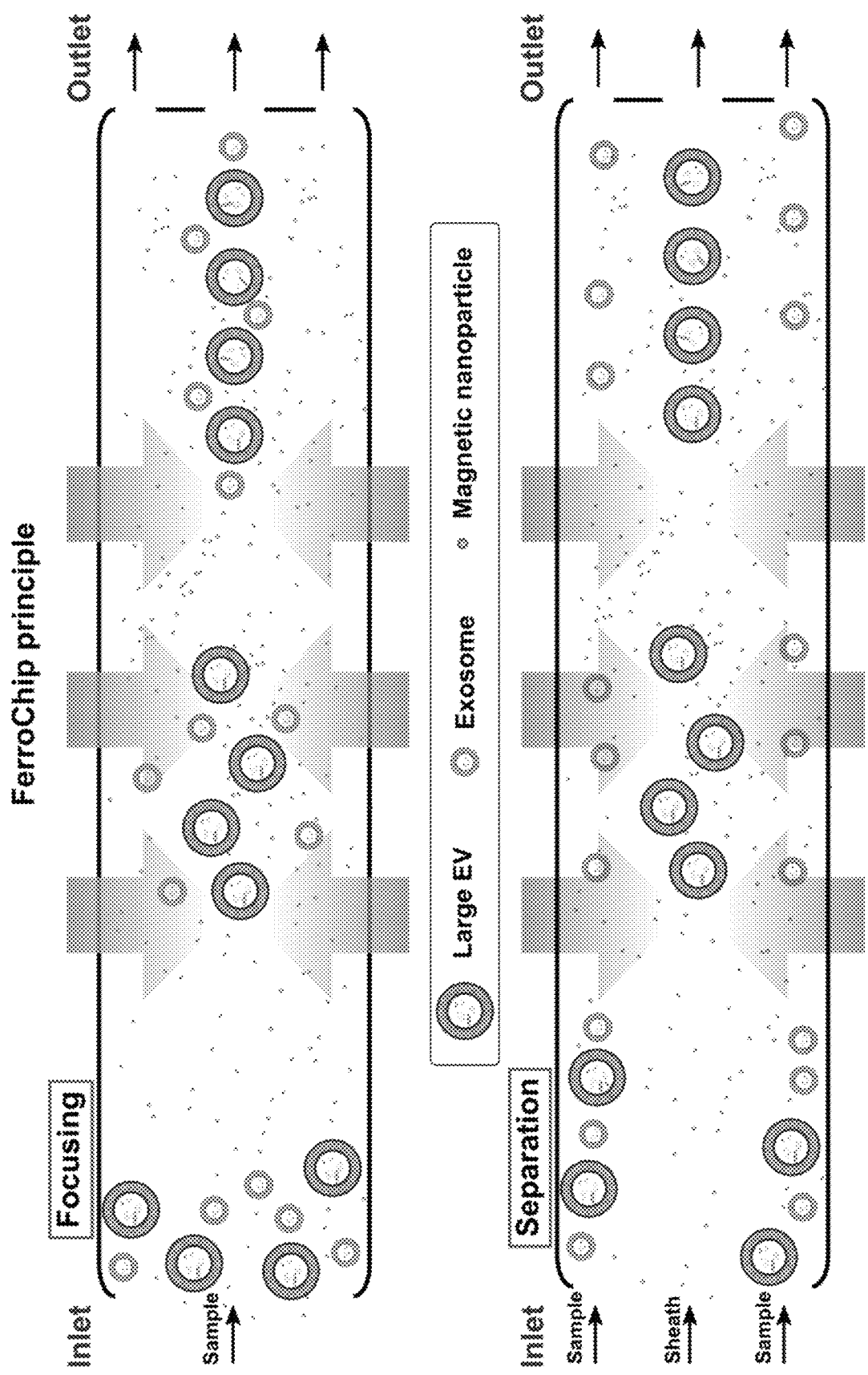

Without the addition of the sheathing ferrofluid, the particles entering the channel in the second stage are spread across the channel and are focused by the magnetic field toward the center of the microfluidic channel such that most of the particles are focused in a stream flowing toward the first outlet, as illustrated in FIG. 1B (top). However, with the addition of the sheathing ferrofluid at the second inlet, where the sheathing fluid is introduced along a central axis (e.g., longitudinal diameter) of the channel of the second stage, this initially results in the sub-micron particles in the mixed sample fluid to flow toward the outer edges or periphery of the channel. Upon flowing through the magnetic field, the sup-population of larger sub-micron particles are focused toward the center of the channel more quickly than the sub-population of smaller sub-micron particles, as shown in FIG. 1B (bottom). Thus the first sub-population of larger sub-micron particles flows along the center of the channel and toward the first outlet, and the second sub-population of smaller sub-micron particles experience a lesser focusing force, leaving them flowing more along the periphery of the channel and toward the second outlet(s).

As described above, in embodiments the fluid sample can be a biological sample, such as blood, blood plasma, or other bodily fluid (e.g., extracellular fluid, urine, wound exudate, etc.). In embodiments, the sample can be blood that has been processed (e.g., centrifuged) to remove blood cells and other components. In embodiment, the sample is a biological sample that has been treated to remove cells and large particles. In other embodiments, cells and/or large particles can be separated in the filter stage. Generally, most blood cells and large particles (protein agglomerates, tissue residue, etc.) are removed prior to introduction to the device to prevent clogging of the device. In embodiments where the sample is a biological sample, the sub-micron sized particles can be exosomes and/or other extracellular vesicles/particles.

As described above, in embodiments of the methods of the present disclosure, the magnetic source in the microfluidic device includes a first and second array of magnets, where the second stage is sandwiched between the first magnet array and the second magnet array, the first magnet array and the second magnet array are in a quadrupole configuration and oriented to repel each other, and the second stage is oriented such that the length of the microfluidic channel in the second stage is substantially centrally aligned between the first magnet array and the second magnet array. In embodiments, the magnetic source is configured to produce a magnetic field flux density that ranges from about 0 to about 0.5T within the microfluidic channel, such that the magnetic field flux density is lower near a central longitudinal axis of the channel and higher near outer portions of the channel. In embodiments, the magnetic source is configured to produce a magnetic field flux density gradient within the channel of about 820 to 1265.

Due to their small size, submicron particles need longer residence time in the microchannel to be focused or separated, therefore the flow rate associated with submicron particles is slower than that of micron particles. Efficient separation can also be a function not only of flow rate, but of ferrofluid concentration, and magnetic field flux density and flux density gradient. As described in the examples below, these parameters were optimized to allow efficient and effective separation for submicron size particles. In embodiments, the ratio of flow rate of the fluid sample (first flow rate) to the flow rate of the sheathing ferrofluid (second flow rate) is about 1:3 to 1:10, such as 1:5. In embodiments, the flow rate of the mixed fluid sample at the first inlet is about 0.01-20 μL/min. In embodiments, it is 0.01-5 μL/min. For the sheathing fluid, in embodiments, the flow rate of the sheathing fluid at the second inlet is about 0.03-200 μL/min, e.g., about 0.05-100 μL/min. In embodiments, the flow rate of the combined sheath/sample is about 0.06-120 μL/min. In embodiments, the flow rate of mixed sample fluid is about 1 μL/min and flow rate of sheathing fluid is about 3-10 μL/min (e.g., about 5 μL/min). As described above, in embodiments of methods of the present disclosure, the mixed sample fluid can have a concentration of magnetic nanoparticles of about 0.01 to 0.6% and the sheathing ferrofluid has a volume concentration of magnetic nanoparticles between about 50% and 90% of the volume concentration of magnetic nanoparticles in the mixed sample fluid.

In embodiments of methods of the present disclosure using the devices of the present disclosure under the operating parameters disclosed, sub-micron particles can be focused and enriched from the fluid sample at a recovery rate of about 94% or more (e.g., 94.3% or more, 95% or more, 97% or more) with a purity of about 87% or more for separation of particles with an average diameter of less than about 200 nm.

For purposes of general comparison of the devices and methods of the present disclosure for focusing and sorting/separation of sub-micron particles vs. devices and methods for separation of micron size particles, the following table provides some exemplary (but not necessarily limiting) parameters:

TABLE 1

| | Submicron particles | Micron particles |
|---|---|---|
| Flow rate of particle suspension into the microchannel: Submicron particles need longer residence time in the microchannel to be focused or separated, therefore the flow rate associated with submicron particles is slower than that of micron particles. | 0.01-20 μL/minute | 10-250 μL/minute |
| External magnetic field flux density. The flux density is lower than that used in micron particles, because of the specific magnet configuration depicted below. | 0-0.5 T | 1.3-1.5 T |
| External magnetic flux density gradient. The gradient of flux density is higher than that used in micron particles, because of the specific magnet configuration depicted below. | 820-1272 T m$^{-1}$ | 0-625 T m$^{-1}$ |
| Magnet configuration and example dimensions | 38.1 mm*6.35 mm*6.35 mm (L*W*H) | 50.8 mm*6.35 mm*6.35 mm (L*W*H) |

TABLE 1-continued

| | Submicron particles | | Micron particles | |
|---|---|---|---|---|
| | S | N | S | N |
| | N | S | N | S |
| | S | N | N | S |
| | N | S | S | N |
| Ferrofluid concentration (v/v) | Mixed Sample: 0.01-0.6% Sheathing: 0.025-0.27% | | 0.024-0.033% | |
| Microchannel parameters | Depth: 50-500 μm Length: 45-57 mm Width: 300-1200 μm | | Depth: 100-500 μm Length: 52-57 mm Width: 1000-1600 μm | |
| Particle size (diameter) | 30-1200 nm | | 3-60 μm | |
| Example Particle type | Diamagnetic submicron particles that have zero or close-to-zero magnetization in the presence of an external magnetic field: submicron inorganic solid particles including polystyrene, silica and other materials; submicron biological particle including exosomes, extracellular vesicles, apoptotic bodies from cells and others. | | Diamagnetic micron particles that have zero or close-to-zero magnetization in the presence of an external magnetic field: micron inorganic solid particles including polystyrene, silica and other materials; micron biological particle including cells, circulating tumor cells, and others. | |

Additional details regarding the methods, compositions, and organisms of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Label-Free Ferrohydrodynamic Manipulations of Submicron Particles and Biological Entities Introduction The present example describes an embodiment of a submicron focusing/separation method based on "particle ferrohydrodynamics" and its associated microfluidic device, termed as the FerroChip. The devices described here can separate exosome-like nanoparticles from microliters of cell culture media and human serum in a label-free, continuous-flow and size-dependent manner, and achieves a high recovery rate (94.3%) and a high purity (87.9%). Separated exosome-like nanoparticles had diameters, morphology and protein expressions that were consistent with other reports. These devices, kits, and methods can facilitate basic understanding of exosomes and provide efficient enriching and sorting devices and methods for clinical application in blood liquid biopsy.

Progress on understanding the communication between tumor cells and their microenvironments are crucial for the development of new diagnostic methods and therapeutic strategies.[1-3] Such communication, traditionally known to occur through direct cell-cell contacts and soluble factor secreted by tumor cells, is now revealed to have an additional mechanism involving extracellular vesicles (EVs).[4,5] EVs consist of a heterogeneous population of lipid-encapsulated vesicles that transmit functional proteins and nucleic acids, with multiple subtypes including exosomes that are extracellular membrane vesicles of endosomal origin, having a physical diameter typically within the range of 30-150 nm.[4-7] Other subtypes of EVs include microvesicles that are shed directly by budding from the cellular plasma membrane, with a physical diameter ranges from 100-1000 nm.[4-7] Growing evidence shows that EVs participate in the metastatic spreading of cancers, in which tumor-derived EVs aid the establishment of pre-metastatic niche and facilitates tumor progression.[8-13] As a result, circulating tumor exosomes containing tumor-specific molecular messages could hold promising clinical utilities as next-generation diagnostic and prognostic biomarkers in liquid biopsy.[4,8,9]

Despite the rapid progress in the understanding of the biology, function, and clinical utilities of extracellular vesicles, the heterogeneous sizes and cargos of these nanoscale vesicles and the technical limitations in separating pure exosomal subpopulation have hindered the characterization of their molecular signatures and its clinical utility. Various strategies have been developed to isolate EV subpopulations, especially exosomes. These strategies include benchtop methods that rely on either differential ultracentrifugation or polymer-based precipitation. Even though these methods can handle milliliters to liters of samples, the recovery rate, purity and integrity of separated exosomes, as well as their labor-intensiveness and long processing time remain to be improved.[6] On the other hand, microfluidic methods emerged as a promising alternative to the benchtop methods in separating exosomes in microliters to milliliters of samples, with high purity or recovery rate while keeping the cost affordable and the processing time short. Technologies of microfluidic exosome separation can be divided into two categories, with the label-based approaches relying on surface markers of exosomes for selective separation of specific exosomal subpopulations with high purity.[14-20] On the other hand, label-free separation explores the size difference between exosomes and other EVs, including deterministic lateral displacement,[21] pinched-flow fractionation,[22] asymmetric-flow field-flow fractionation,[23] filtration,[24] nanowire trapping,[25,26] viscoelastic separation,[27] and acoustic separation.[28] Label-free separation of exosomes was not biased by the use of specific biomarkers and therefore could lead to exosome separation with high recovery rate. The present example reports a new label-free ferrohydrodynamic method for high recovery and purity separation of exosome-like nanoparticles, which are defined as having diameters of about 30-150 nm, and morphology and protein expressions consistent with exosomes. This method relies on the physical principle of "particle ferrohydrodynamics" and can separate exosome-like nanoparticles from biological samples with about a 94.3% recovery rate and about 87.9% purity.

Ferrohydrodynamics describes the mechanics and motion of a magnetizable liquid (e.g., ferrofluids) influenced by strong forces of magnetic polarization.[29] The present example explores "particle ferrohydrodynamics" that refers to the mechanics and motion of an immersed diamagnetic object (either a solid particle or an extracellular vesicle) with close to zero magnetic susceptibility in a magnetizable liquid under an externally applied magnetic field. Particle ferrohydrodynamics is a physical process that drives the immersed object's movement as a result of the interaction between the magnetic field and the magnetic liquid surrounding the object. The magnetic liquid itself, often a ferrofluid, consists of a colloidally stable suspension of magnetic nanoparticles. Under a non-uniform magnetic field, these magnetic nanoparticles exhibit a gradient of particle concentration while maintaining its stability against irreversible agglomeration thanks to the surfactants on their surfaces. In the particle ferrohydrodynamic process, the magnetic nanoparticles within a ferrofluid continuously collide with the immersed diamagnetic object and generate pressure across the object's surface. This leads to an imbalance of pressure across the object's surface, and a net movement of the object in the opposite direction of nanoparticle concentration, as well as the magnetic field gradient. This phenomenon of an immersed diamagnetic object moving in the opposite direction of the magnetic field gradient is referred to as "diamagnetophoresis" or "negative magnetophoresis" in the literature.[30] Particle ferrohydrodynamics was applied in microfluidic systems for micron-sized particle and cellular manipulation, such as isolating extremely rare circulating tumor cells from cancer patients' blood.[31, 32] However, ferrohydrodynamic particle manipulation was thought to be limited to micron-sized objects, because the carrier magnetic liquid includes nanoparticles with a diameter of ~10 nm. It was thought that the size of the immersed object needed to be significantly larger than the magnetic nanoparticles themselves. Indeed, the smallest objects that were experimentally manipulated in ferrofluids to date was limited to 1 µm, such as polymer particles of 1 µm in diameter,[33] and *Escherichia coli* cells with the short axis of 0.5-1 µm and the long axis of 2-4 µm.[34] The present example successfully demonstrated a label-free ferrohydrodynamic method that can separate exosome-like particles with diameters of 30-150 nm from biological samples. To the best of our knowledge, this is the first time that nano-sized particles were separated via "particle ferrohydrodynamics" in microfluidic devices.

As will be described in detail below, first the theoretical limit of the smallest particles that could be manipulated via particle ferrohydrodynamics was calculated, and then the feasibility of applying particle ferrohydrodynamics in microfluidic setting for exosomal separation was determined. We then developed a prototype device termed as the FerroChip, performed systematic optimization of key factors influencing the performance of the FerroChip, and determined parameters for high purity and recovery rate exosomal separation. Finally, we challenged the FerroChip with both cell culture media and human serum for its ability to separate exosome-like nanoparticles.

Materials and Methods

Ferrohydrodynamic Modeling in Microfluidic Devices

A previously developed analytical model was adopted in this study to simulate the trajectories of immersed nanoparticles/EVs in ferrofluids in a three-dimensional (3D) manner (incorporated by reference herein).[31, 47] This model provides a fast prediction of three-dimensional ferrohydrodynamic transport of nanoparticles and EVs inside a microfluidic channel coupled with quadruple configurations of permanent magnets. Trajectories of the nanoparticles/EVs in the FerroChip were obtained by (1) first computing the three-dimensional magnetic force via an experimentally verified and analytically computed distribution of magnetic fields as well as their gradients, together with a nonlinear Langevin magnetization model of the ferrofluid that considers ferrofluids to be a continuous medium, and the magnetic nanoparticles inside the ferrofluid to be non-interacting, (2) secondly computing the ferrohydrodynamic motion of diamagnetic nanoparticles/EVs through the governing equations of nanoparticles/EVs in laminar flow conditions, using analytical expressions of magnetic forces and hydrodynamic viscous drag forces. The script for this model was developed and solved in MATLAB (MathWorks Inc., Natick, MA).

Ferrofluids Synthesis, Characterization and Composition

Water-based ferrofluid with maghemite nanoparticles was synthesized by a chemical co-precipitation method following an established protocol.[47] Transmission electron microscopy (TEM; FEI, Eindhoven, the Netherlands) were used to characterize the size and morphology of maghemite nanoparticles. The viscosity of ferrofluids was measured with a compact rheometer (Anton Paar, Ashland, VA) at room temperature. Magnetic properties (volume fraction of magnetic materials and saturation magnetization) of the ferrofluid were characterized using a vibrating sample magnetometer (VSM; MicroSense, Lowell, MA). The diameter distribution of the maghemite nanoparticles in the ferrofluid is 10.91±4.86 nm. The surfactant on the nanoparticles is a graft copolymer (Atlox 4913, Croda, Inc., Edison, NJ). Ferrofluid was adjusted to biocompatible by changing the pH to 7 with sodium hydroxide and balancing the osmotic pressure with Hank's Balanced Salt Solution (Thermo Fisher Scientific, Waltham, MA). The concentration of ferrofluid was measured to be 0.3% (v/v) and the corresponding viscosity of this ferrofluids was 1.68 mPa·s at 23° C.

Cell Culture and Extracellular Vesicles Preparation

Extracellular vesicles were prepared from cell lines: human breast cancer (MDA-MB-231, ATCC, Manassas, VA) and lung cancer (A549, ATCC, Manassas, VA). Cell lines were cultured following the manufacturer's recommended protocol. The culture medium was supplemented with 10% exosome-free FBS (Thermo Fisher Scientific, Waltham, MA). The extracellular vesicles were isolated from the cell culture supernatant. The collected supernatant was centrifuged at 500 g for 5 minutes to remove cells. To collect extracellular vesicles smaller than 800 nm, the supernatant was processed by membrane filtration (800 nm pores, Pall Corporation), followed by adding 20% ExoQuick-TC reagent (System Biosciences, CA). The mixture was incubated overnight at 4° C., followed by centrifugation at 1,500 g for 30 minutes. Extracellular vesicles were resuspended in 200 µL using sterile 1×PBS. To collect large extracellular vesicles (diameters: 200 nm to 1000 nm), the collected culture supernatant was processed by centrifugation at 12,000 g for 90 minutes at room temperature. Large extracellular vesicles were collected by resuspending the pellet in 200 µL 1×PBS. Smaller exosomes (diameters: 30 nm to 150 nm) were obtained by mixing the remaining supernatant with 20% ExoQuick-TC reagent, following the manufacturer's protocol. The exosomes were resuspended in 200 µL 1×PBS. The extracellular vesicles (both large extracellular vesicles and small exosomes) were then fluorescently stained with PKH 67 or PKH 26 (Sigma-Aldrich, St. Louis, MO) following the manufacturer's protocol.

FerroChip Fabrication and Assembly

The microfluidic channel of the FerroChip contains a filtration channel and particle manipulation (focusing or separation) channel. Using standard soft lithography techniques, the devices were made of polydimethylsiloxane (PDMS) with a channel height of 150 µm, measured by a profilometer (Veeco Instruments, Chadds Ford, PA). The fabricated microchannel was placed in the quadrupole permanent magnet array and held in a custom-made aluminum manifold. Each magnet was 38.1 mm in length, 6.35 mm in both width and thickness, with a residual magnetic flux density of 1.48 T.

Microfluidic Experiment Setup and Procedure

The FerroChip was first flushed by 70% ethanol for 10 minutes, followed by priming with 1×PBS supplemented with 0.5% (w/v) bovine serum albumin (BSA) and 2 mM EDTA (Thermo Fisher Scientific, Waltham, MA) for 10 minutes with a flow rate of 100 µL/min. Sample ferrofluids that contained polystyrene particles or extracellular vesicles were supplemented with 0.5% (w/v) BSA to prevent particle aggregation. Sample fluids and sheath fluids were injected into the microfluidic inlets using individually controlled syringe pumps (Chemyx, Stafford, TX) at variable flow rates. The FerroChip was placed on the stage of an inverted microscope (Axio Observer, Carl Zeiss, Germany) for observation and recording. Images and videos of particles were obtained from a CCD camera (Carl Zeiss, Germany).

Removal of Magnetic Nanoparticles From Exosomes

After FerroChip processing and before characterizations, the maghemite nanoparticles in ferrofluids could be removed by increasing the pH of the ferrofluid to 7.5-8 with sodium bicarbonate. Briefly, the sample was collected in an Eppendorf tube and the tube was placed into a customized magnet array. 0.1 M NaHCO3 was added into the solution until its pH reached to 7.5-8. The solution was incubated for 3 hours at room temperature. The maghemite nanoparticles formed clusters and were attracted by the magnet array. Supernatant of the solution was removed, and the resulted solution was centrifuged at 1000 g for 5 minutes to further remove nanoparticle clusters.

Extracellular Vesicles Characterization

Dynamic Light Scattering (DLS). Polystyrene submicron particles were measured by a Zetasizer Nano ZS Analyzer (Malvern Panalytical Ltd, United Kingdom). 5 μL of the collected sample from FerroChip outlets was diluted with 20 mL filtered DI water and measured at room temperature.

Atomic Force Microscopy (AFM). Collected extracellular vesicles were imaged by a multimode-8 AFM (Bruker, Billerica, MA) using the tapping mode with the DNP-S10 probe.

Super-Resolution Microscopy. Collected extracellular vesicles were imaged by a Zeiss ELYRA S1 (SR-SIM) super-resolution microscope (Carl Zeiss, Germany).

Transmission Electron Microscopy (TEM). Collected extracellular vesicles were fixed with 2% paraformaldehyde for 10 min at room temperature and then dropped onto electron microscope grids. After incubation for 20 min, the grids were transferred to a 50 μL drop of 2.5% glutaraldehyde in sodium cacodylate buffer for 10 min. The grid was transferred to a 100 μL drop of filtered distilled water and washed 3 times. After drying for 20 min, the extracellular vesicles were stained with 1% uranyl acetate for 1 min. Collected extracellular vesicles were imaged by JEOL JEM1011 (JOEL, Inc., Peabody, MA) transmission electron microscope (TEM) at 80 kV.

Western Blot. Exosomes collected from the side channel of the FerroChip were lysed using RIPA buffer with protease inhibitor cocktail added. The protein concentration was quantified using a standard Bradford protein assay and 20 μg of protein was loaded for each well. Laemmli buffer (with Beta-mercaptoethanol) was added and the sample was heated at 95° C. for 5 minutes and chilled on ice before loading onto gel (Bio-Rad Laboratories, Hercules, CA). Standard SDS-PAGE electrophoresis was performed, and the protein lysates were transferred onto PVDF membrane (Santa Cruz Biotechnology, Inc., Dallas, TX). The membrane was then incubated overnight with exosome primary antibodies against CD63 and HSP70 (Santa Cruz Biotechnology, Inc., Dallas, TX following incubation with Goat-Rabbit-HRP secondary antibody (Santa Cruz Biotechnology, Inc., Dallas, TX). Blot was incubated with Western ECL substrate (Bio-Rad Laboratories, Hercules, CA) to enhance the signal, and the blot was visualized with ChemiDoc MP Imaging System (Bio-Rad Laboratories, Hercules, CA).

Healthy Subject Blood Sample Preparation. Human whole blood from a healthy subject (Zen-Bio, Research Triangle, NC) was purchased and centrifuged at 3,000 g for 15 minutes to remove cells. The supernatant was mixed with a ferrofluid (volume fraction 0.6%) with a 1:1 ratio. Pluronic F-68 non-ionic surfactant (Thermo Fisher Scientific, Waltham, MA) was added before processing.

Immunofluorescence Staining of Exosomes. Isolated exosomes from human blood were plated onto a poly-L-lysine coated glass slide with a customized cell collection chamber for 24 hours at 4° C. The collected exosomes were fixed with 4% (w/v) PFA solution (Santa Cruz Biotechnology, Inc., Dallas, TX), following permeabilization with Triton X-100 buffer (Alfa Aesar, Haverhill, MA) for 10 minutes. The nonspecific binding sites of exosomes were blocked with a blocking reagent (Santa Cruz Biotechnology, Inc., Dallas, TX) before immunostaining with primary antibodies, including anti-EpCAM, anti-CD24, and anti-CD63 (Santa Cruz Biotechnology, Inc., Dallas, TX). The stained exosomes were washed with PBS and covered with mounting medium before imaging.

Results and Discussion

Ferrohydrodynamic Nanoparticle Manipulation

This example estimated the smallest nanoparticle that can be ferrohydrodynamically manipulated by comparing quasi-static effects originated from thermal diffusion and ferrohydrodynamic motion, assuming that (1) ferrofluids are a continuous magnetic medium without significant phase separation under an externally applied magnetic field, and (2) the concentration of ferrofluids is small enough so that interparticle interaction can be neglected (FIG. 1A). Ferrofluids at room temperature are colloidal suspensions of magnetic nanoparticles that are stable against externally applied magnetic fields because the magnetic nanoparticles are on the order of 10 nm in diameter. Ferrofluids used in this study had a volume fraction of magnetic materials of 0.3%, therefore they could be considered non-interacting. The theoretical estimate considers a one-dimensional case with a ferrofluid suspension of height L, and immersed particles uniformly dispersed along L. The characteristic time of an immersed diamagnetic object migrating across L is determined by the shorter of either diffusive time $\tau_D$ or ferrohydrodynamic migration time $\tau_M$. The diffusion time of the immersed object in ferrofluids is $\tau_D = L^2/2D$, where $$D = \frac{k_B T}{3\pi \eta d}$$

is the diffusion coefficient, d is diamagnetic object's diameter, η is ferrofluid viscosity, T is temperature, and $k_B$ is Boltzmann constant. Ferrohydrodynamic migration time of the same diamagnetic object is determined by the Stokes velocity through solving $3\pi\eta d v_M + F_M = 0$, where $F_M = -\mu_0 V (M \cdot \nabla)H$ is ferrohydrodynamic force acting on the particle, $\mu_0$ is permeability of free space, V is object's volume, M is non-linear magnetization of the dilute ferrofluid that is typically modeled through a Langevin function, and H is magnetic field strength at the center of the particle. This yields a characteristic time associated with ferrohydrodynamic motion $\tau_M = l \times L/D$, where $$l = \frac{k_B T}{F_M}$$

has the dimension of length and is indicative of the spatial scale of ferrohydrodynamic migration. The total characteristic time τ of the diamagnetic object migrating across length L is thus $$\tau = \frac{\tau_D \times \tau_M}{\tau_D + \tau_M}.$$

The faster process, whether it is diffusive or ferrohydrodynamic, decides the actual time τ. When $\tau_D = \tau_M$, one obtains the critical diameter of the diamagnetic object that experiences both diffusion and ferrohydrodynamic migration equally, which is $$d = \left(\frac{12 k_B T}{\pi \mu_0 L M \nabla H}\right)^{\frac{1}{3}}.$$

FIG. 1A shows that this critical diameter at room temperature (about 23° C.) is about 30 nm, calculated from relevant parameters in a typical microfluidic setting, including a migration distance L=500 μm, a ferrofluid magnetization M=~1100 A/m, corresponding to the 0.3% (v/v) maghemite particle based ferrofluid used in this study, and a gradient of magnetic field strength $\nabla H$=~8×10$^8$ A/m$^2$, corresponding to a gradient of flux density $\nabla B$=1000 T/m. However, FIG. 1A shows that for a diamagnetic nanoparticle of 30 nm diameter to migrate across 500 μm distance, the estimated characteristic time would be unrealistically long (on the order of 10$^4$ seconds) in a microfluidic device. On the other hand, when the nanoparticle diameter increases to ~100 nm, ferrohydrodynamic motion becomes a much faster process than diffusion, leading to a significant reduction of the characteristic time to the order of ~10$^1$-10$^2$ seconds, making it feasible to manipulate them in microfluidic devices. These theoretical estimates of nanoparticle sizes and characteristic times in particle ferrohydrodynamics, taken together with the constraints from the operation of microfluidic devices, demonstrates that it is possible to ferrohydrodynamically separate diamagnetic nanoparticles that have diameters in the range of 100-1000 nm, and also offers guidance on designing optimal microfluidic devices for this purpose.

Overview of FerroChip Design and Operation

Figure 1C:
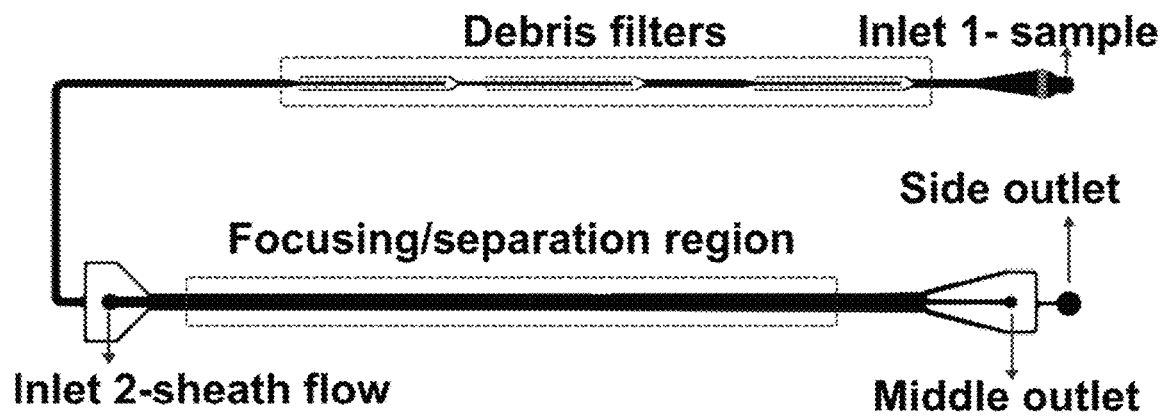
Figure 1D:
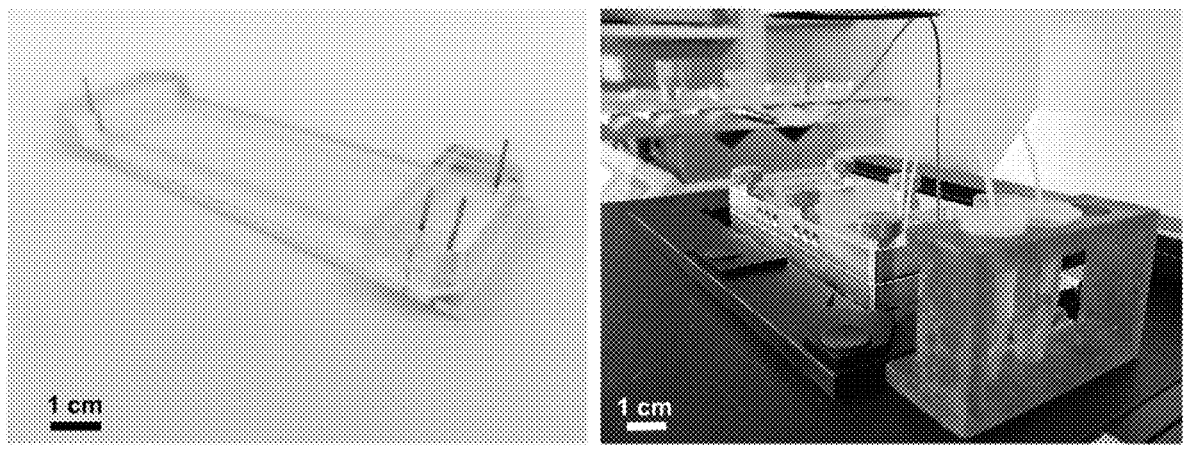

An embodiment of a microfluidic device, referred to herein as FerroChip, which incorporated the particle ferrohydrodynamic working principle, was designed to effectively either focus/enrich or separate/sort diamagnetic nanoparticles based on their size alone. FIG. 1B illustrates the device design of a prototype FerroChip. In the focusing mode of device operation (FIG. 1B, top panel), samples of either diamagnetic nanoparticles or extracellular vesicles (EVs) are premixed with a dilute ferrofluid and enter a straight microchannel with a uniform distribution across the channel width. A quadrupole array of permanent magnets (see FIG. 2B) generates a three-dimensional magnetic field pattern that will result in ferrohydrodynamic migration of diamagnetic nanoparticles or EVs towards the center of the microchannel, effectively focusing them into a narrow stream. In the separation/sorting mode of operation (FIG. 1B, bottom panel), premixed samples of diamagnetic nanoparticles or EVs with ferrofluids enter the straight microchannel through predominately the regions close to the channel wall, due to the effect of a ferrofluid sheath flow. The three-dimensional magnetic field will lead to a size-dependent ferrohydrodynamic migration of nanoparticles or EVs towards the center of the microchannel. Larger diamagnetic nanoparticles or EVs migrate with a faster speed while smaller ones with a slower speed, resulting in a spatial separation of the subpopulations of differently sized objects at the outlets of the channel. FIGS. 1O and 1D show the prototype microchannel that is capable of both nanoparticles and EVs focusing and separation and an assembled FerroChip in use.

The theoretical estimate of size-dependent characteristic time presented above provided a framework for understanding the dominant effects in particle ferrohydrodynamics. Ferrohydrodynamic motion of particles becomes the dominant effect at room temperature as the diameter of particles exceeds ~100 nm. With the FerroChip, the particle ferrohydrodynamic principle is applied to focus or separate diamagnetic nanoparticles or EVs in ferrofluids. For that purpose, the performance of the FerroChip was characterized using three metrics, including the nanoparticle/EV-processing throughput, nanoparticle/EV recovery rate, nanoparticle/EV purity after processing, which were consistently used and reported in evaluating exosome isolation techniques,[6,35] For the FerroChip, the parameters affecting these three metrics include device geometry, magnetic field and its gradient, sample flow rates, and ferrofluid properties. These parameters were coupled and needed to be optimized systematically. Hence, a physical model was developed that takes into consideration the effects of particle ferrohydrodynamics in microfluidic settings, which allowed optimization of relevant device geometries and operating parameters. This physical model predicted three-dimensional (3D) trajectories of diamagnetic nanoparticles or EVs under laminar flow conditions inside a microchannel. Ferrohydrodynamic force and hydrodynamic drag force were considered in simulating the particle trajectories. In the simulation, we chose to neglect the diffusive effect because the diffusive effect starts to become weaker than the ferrohydrodynamic effect when the diamagnetic particle diameter exceeded ~30 nm (FIG. 1a). For instance, the diffusive time is ~36 times longer than the ferrohydrodynamic migration time for a diamagnetic particle of 100 nm in diameter. Because the diameter range of the diamagnetic particles in this study is 30-1000 nm, we can neglect the diffusive effect in our model while still simulate the particle migration accurately. This model provided analytical and quick design optimization to determine the above-mentioned variables and parameters depending on the design constraints.

Validation of Ferrohydrodynamic Motion Through Nanoparticles Focusing.

The ferrohydrodynamic manipulation in the FerroChip was first validated through focusing nanoparticles of diameters ranging from 100 nm to 1000 nm, with a goal of understanding the size-dependence of ferrohydrodynamic particle migration at relevant sample flow rates (1-10 μL/minute). The range of sample flow rates represents typically reported data from existing microfluidic EVs separation technologies.[6-35] The range of particle diameters (100-1000 nm) coincides with major populations of EVs that include microvesicles (100-1000 nm) and exosomes (30-150 nm).[5-7]

Figure 2A:
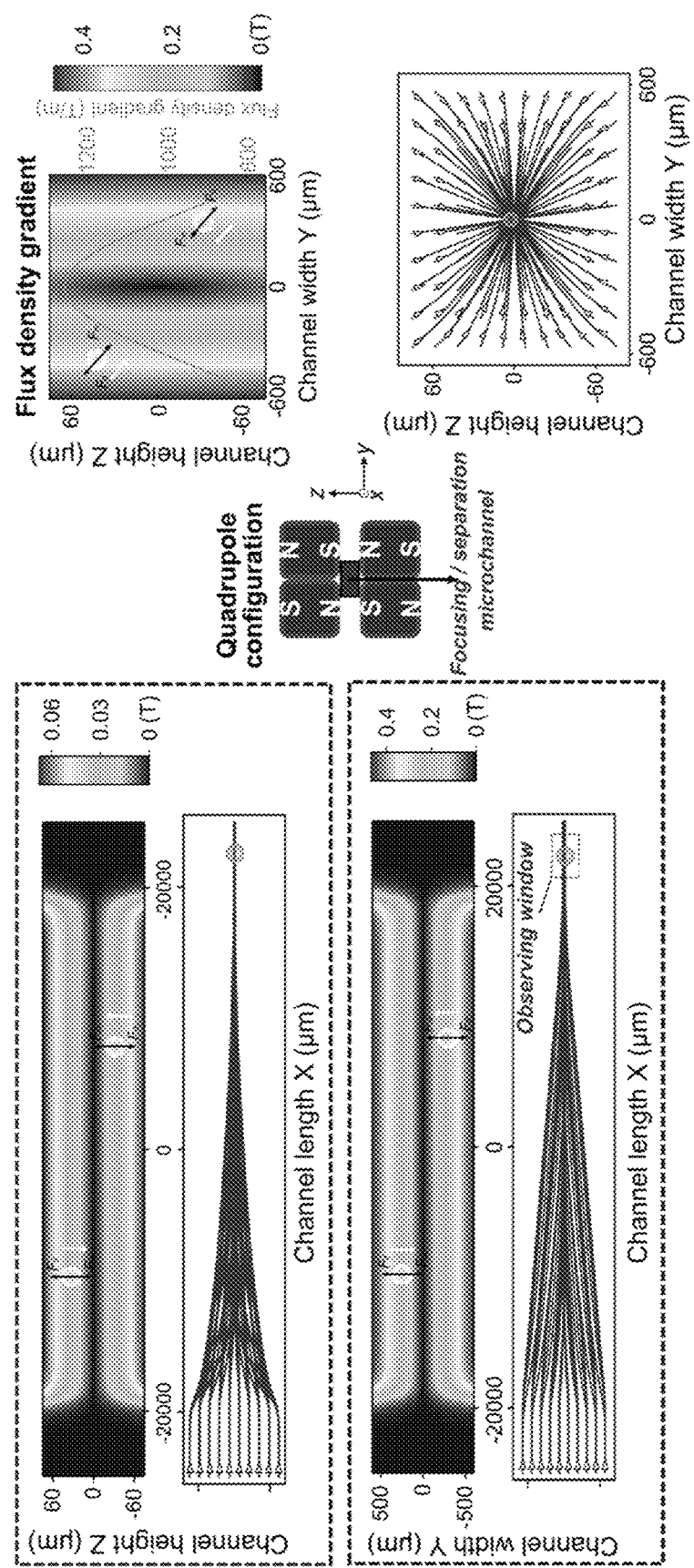
FIGS. 2A-2B illustrate system optimizations of the FerroChip for continuous-flow nanoparticle focusing.
Figure 2B:
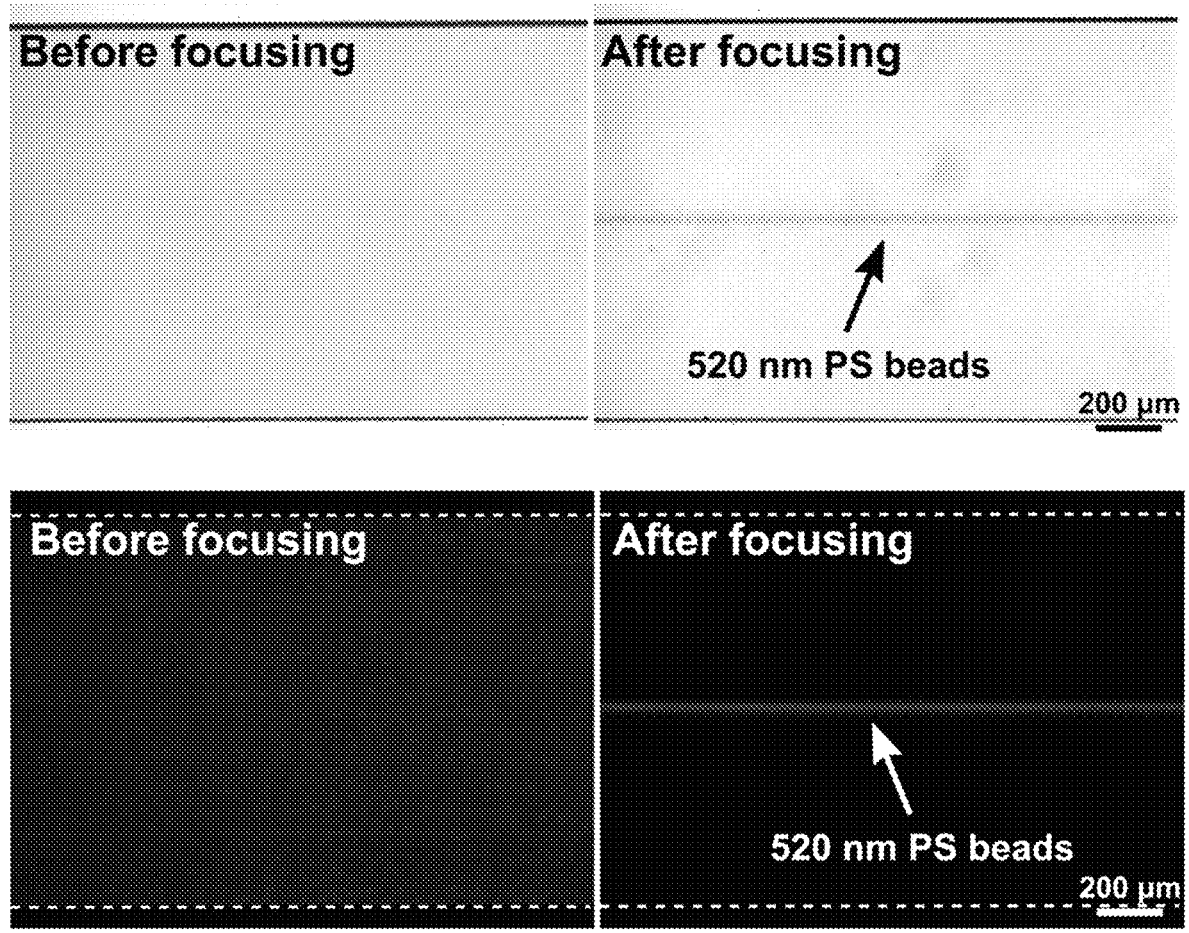
Figure 10:
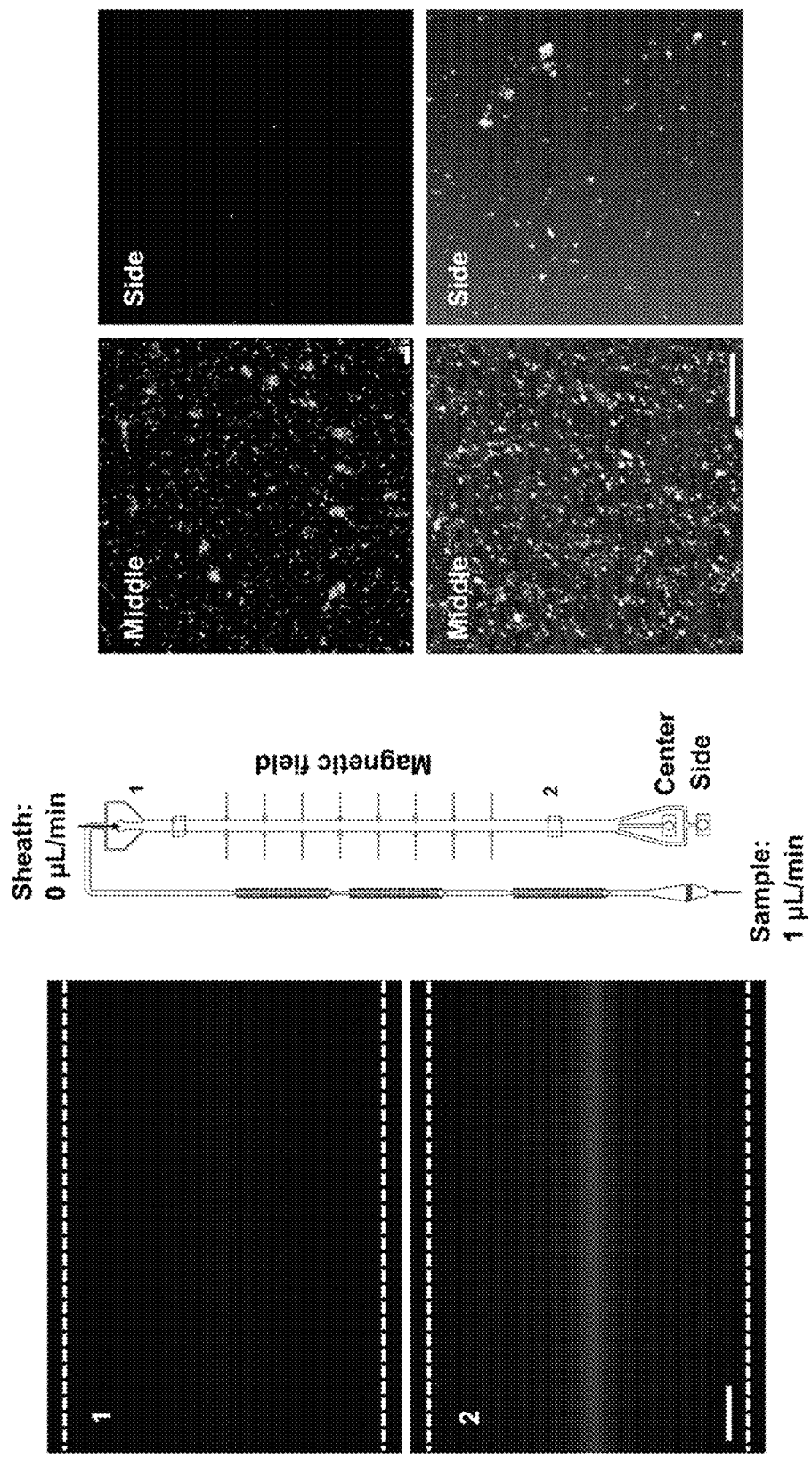
FIG. 10 provides AFM images of extracellular vesicles (EVs) in the FerroChip separation experiment using MDA-MB-231 breast cancer cell culture media from FIG. 5A-5E in the main text. AFM images of the sample before separation (left, mixture of exosomes and large EVs) and sample after separation (right, EVs collected from side outlet) (channel configuration in center) showed a clear size difference. Sample flow rate is 1 µL min$^{-1}$, and sheath flow rate is 5 µL min$^{-1}$. Scale bar: 1 µm.

Validation focused on the effects of device geometry, magnetic field, and its gradient, sample flow rates, as well as ferrofluid concentration on the effect of diamagnetic nanoparticle focusing. Firstly, we determined the dimension of focusing region of the microchannel by balancing a need of processing ~100 μL of EVs sample within one hour, and a need to maintain laminar flow in the device. Final microchannel dimensions (55×1.2×0.15 mm, L×W×H) were optimized so that Reynold's number was on the order of 0.03 when the sample flow rate was 100 μL h$^{-1}$, ensuring laminar flow condition. The prototype microchannel is shown in FIG. 10. Secondly, the amplitude of ferrohydrodynamic force on diamagnetic nanoparticles is proportional to the amplitude of the magnetic field gradient. In order to maximize the field gradient, a quadrupole magnet configuration was adopted in the FerroChip design that could be optimized to generate the needed magnetic flux density and its gradient. Using four permanent magnets (38.1 mm by 6.35 mm by 6.35 mm, N52 neodymium magnet) in a quadrupole configuration shown in FIG. 2A (center), a magnetic flux density of up to 0.5 T in the x-y plane (z=0), and a magnetic flux density gradient of 1272 T m$^{-1}$ in the y-z plane (x=0) were obtained. Under the magnetic field of the quadrupole magnets, simulation of trajectories of 520 nm polystyrene particles in ferrofluids were conducted to study the effectiveness of FerroChip in focusing these particles. A sample inlet flow rate of 3 µL min$^{-1}$ and a ferrofluid concentration of 0.3% (v/v) were used in the simulation. Results in FIG. 2A show that 520 nm particles could be focused in all three dimensions in the prototype device. Experimental results in FIG. 2B confirmed that ferrohydrodynamic effects under this quadrupole magnet configuration were significant enough so that 520 nm particles were successfully focused into a narrow stream in the FerroChip.

Figure 3A:
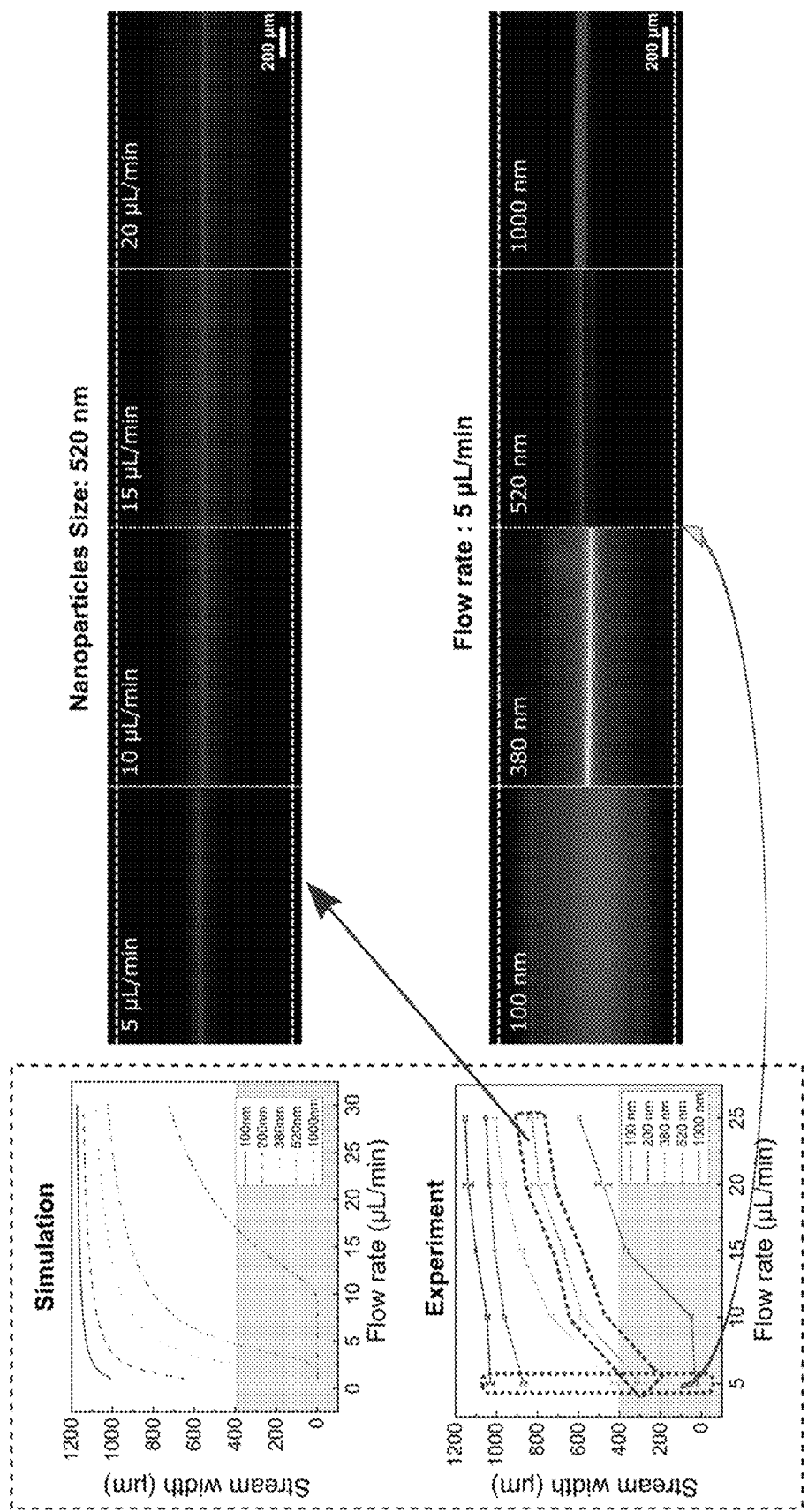
FIGS. 3A and 3B illustrate optimizations of nanoparticle focusing in the FerroChip, with parameters including particle diameter, flow rate, and ferrofluid concentration.
Figure 3B:
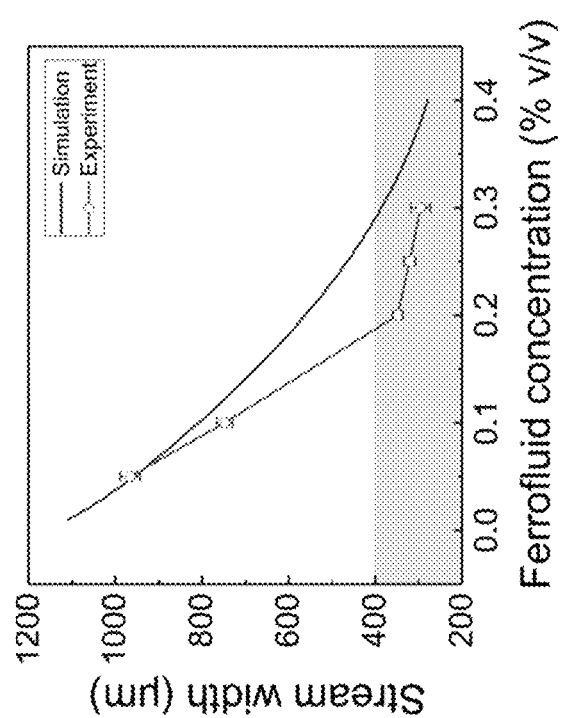
Figure 3B:
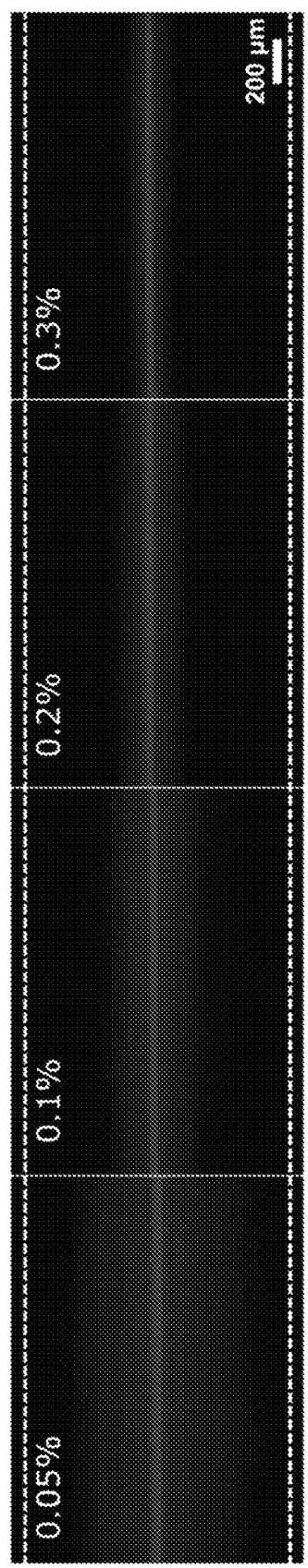

The remaining study explored the effect of sample flow rates and ferrofluid concentration on the focusing effect. We defined an output—the width of focused diamagnetic particle streams (see FIG. 2A for coordinates) as a way to quantify the focusing effect. This output was optimized using parameters including sample flow rates (1-30 µL min$^{-1}$) and ferrofluid concentrations (0-0.4% v/v). The goal was to maximize the focusing effects, which translated to minimizing the stream width. FIG. 3A shows that simulation and experimental data agreed reasonably well, and both of which indicated that the stream widths had a monotonic relationship with the flow rates. Faster flow rates reduced the residual time of diamagnetic nanoparticles in the microchannel, thereby decreasing the ferrohydrodynamic migration of the particles, which in turn increased the particle stream width. As the size of diamagnetic nanoparticle increased, the width of stream decreased since ferrohydrodynamic force is proportional to the volume of diamagnetic particles. The ferrofluid concentration was further optimized, and it was found that a higher concentration could lead to a higher magnitude of the diamagnetic force on nanoparticles therefore a larger focusing effect (FIG. 3B).

Optimization of FerroChip for Exosome-Like Nanoparticles Separation.

FerroChip design was then optimized as well as its operating parameters for label-free separation of exosomes in biological fluids, with a goal of sorting/isolating exosomes based on their size differences from large extracellular vesicles. The range of diameters of exosomes (30-150 nm) was reported to be smaller than that of apoptotic bodies (>1000 nm) and microvesicles (100-1000 nm).[5-7] This size difference between exosomes and other extracellular vesicles was utilized for a high recovery rate and purity separation of exosomes with a clinically relevant throughput. In quantitative terms, the performance goals for the FerroChip included: (1) an exosome recovery rate of >90%; (2) a sample processing throughput of ~1 µL min$^{-1}$, and (3) a purity of exosome of >90% after separation. These metrics were chosen as performance targets after a survey of existing microfluidic exosome separation methods.[6,35]

Figure 4A:
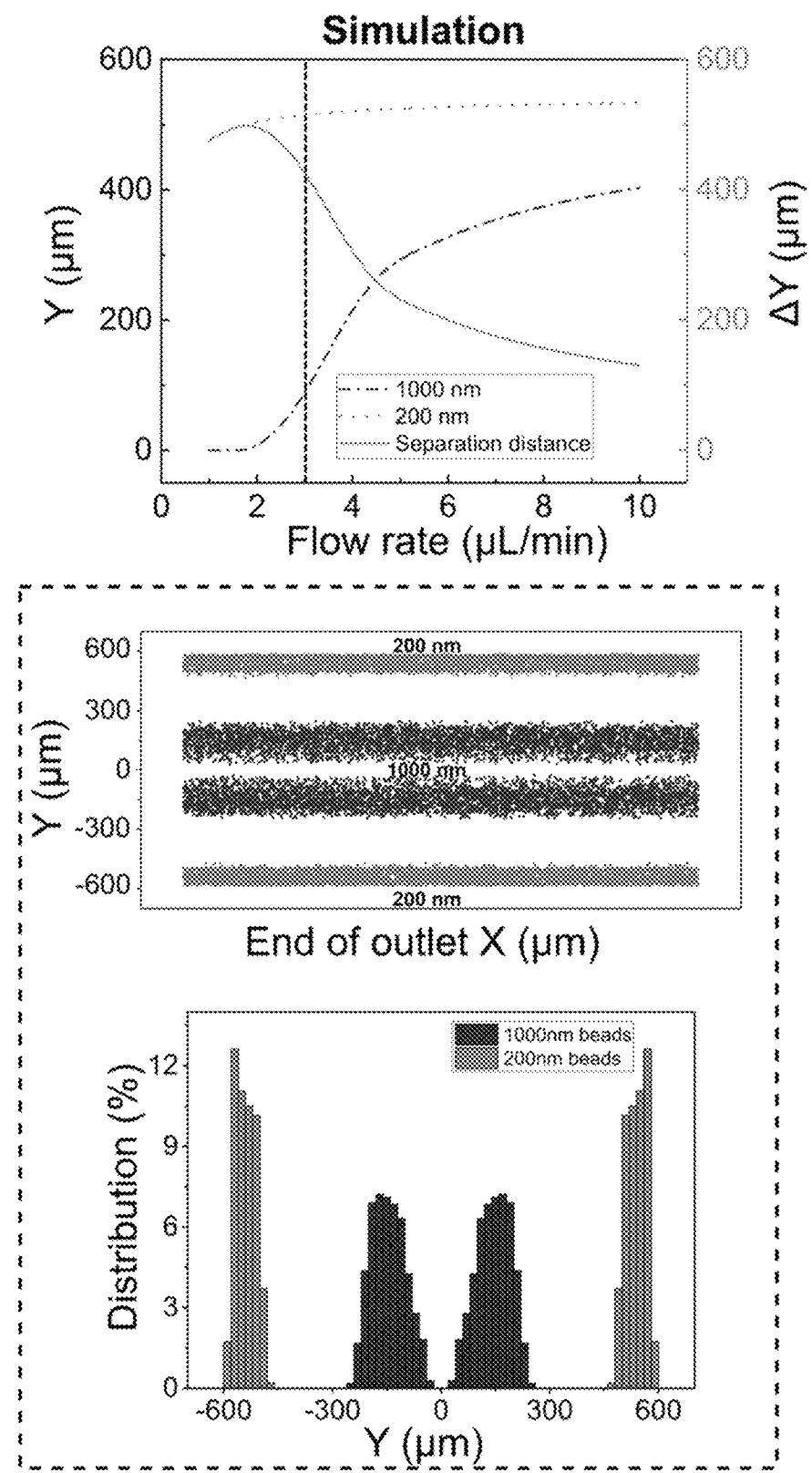
FIGS. 4A-4C illustrate optimizations of the FerroChip for the separation of exosome-like nanoparticles (30-150 nm in diameter) from large extracellular vesicles (200-1000 nm in diameter).

Through the optimization of FerroChip design and its operating parameters in the previous section, the following parameters were determined to be appropriate for exosome separation. (1) FerroChip device geometry and dimensions: the top view of the device is depicted in FIG. 1C, with optimized channel dimensions (55×1.2×0.15 mm, L×W×H) for laminar flow condition and clinically relevant throughput. (2) Magnetic field parameters: a magnetic flux density of up to 0.5 T, and a magnetic flux density gradient of up to 1272 T m$^{-1}$ were achieved via assembling four neodymium permanent magnets in quadrupole configuration. (3) Ferrofluid concentration: a 0.3% volume fraction of maghemite nanoparticle based ferrofluid was used. The corresponding viscosity of this ferrofluid was 1.68 mPa·s at 23° C. (4) Sample flow rates: exosomes were represented by 200 nm particle, and other larger extracellular vesicles were represented by 1000 nm particles. The mean diameter of exosomes was chosen to be slightly larger than 150 nm to ensure all particles smaller than 200 nm to be separated from larger extracellular vesicles. With these two diameters, simulations demonstrated that a sample flow rate of 3 µL minute$^{-1}$, and a sheath flow rate of 15 µL minute$^{-1}$, would yield significant separation of the two species in the FerroChip (FIG. 4A). For the simulations, two outputs were calculated—a deflection in the y-direction for EVs (see FIG. 2A for coordinates), denoted as Y, and a separation distance between exosome (200 nm) and large EVs (1000 nm), denoted as ΔY. Both outputs were optimized using a sample flow rate of (0-10 µL min$^{-1}$, i.e., 0-600 µL h$^{-1}$). The goal was to maximize the exosome recovery rate and minimize large EV contamination, which translated to maximizing ΔY and the flow rate simultaneously. FIG. 4A shows that separation distance ΔY was close to the maximum when using a ferrofluid with 0.3% magnetic volume fraction, and a flow rate of 3 µL min$^{-1}$ (i.e., 180 µL h$^{-1}$). FIG. 4A also shows a distribution of simulated EV locations at the outlets. The distribution confirms that 200 nm exosomes and 1000 nm large EVs can be ferrohydrodynamically separated in the FerroChip, and 100% of exosomes can be recovered with none of the large EV contamination.

Figure 4B:
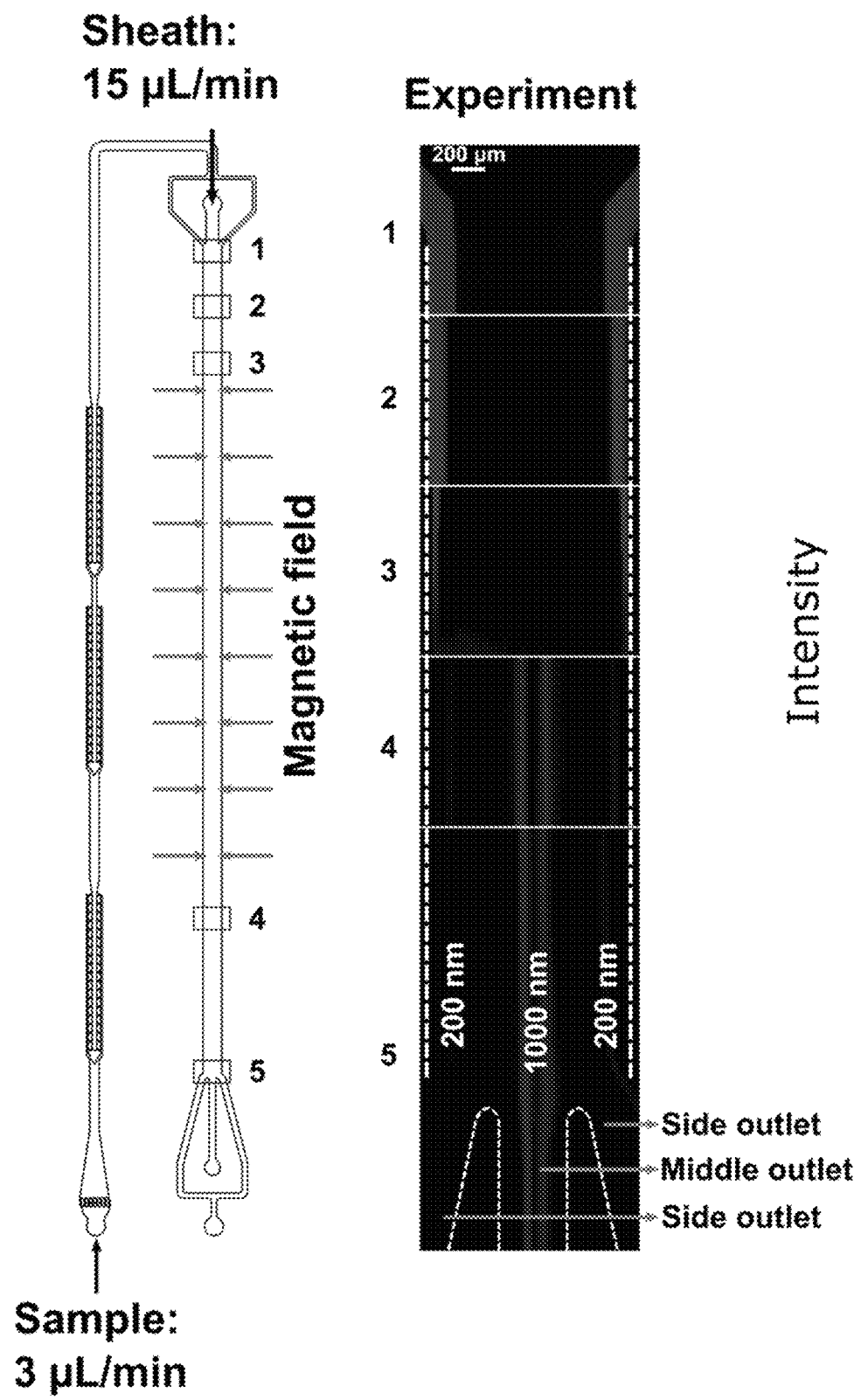
Figure 4C:
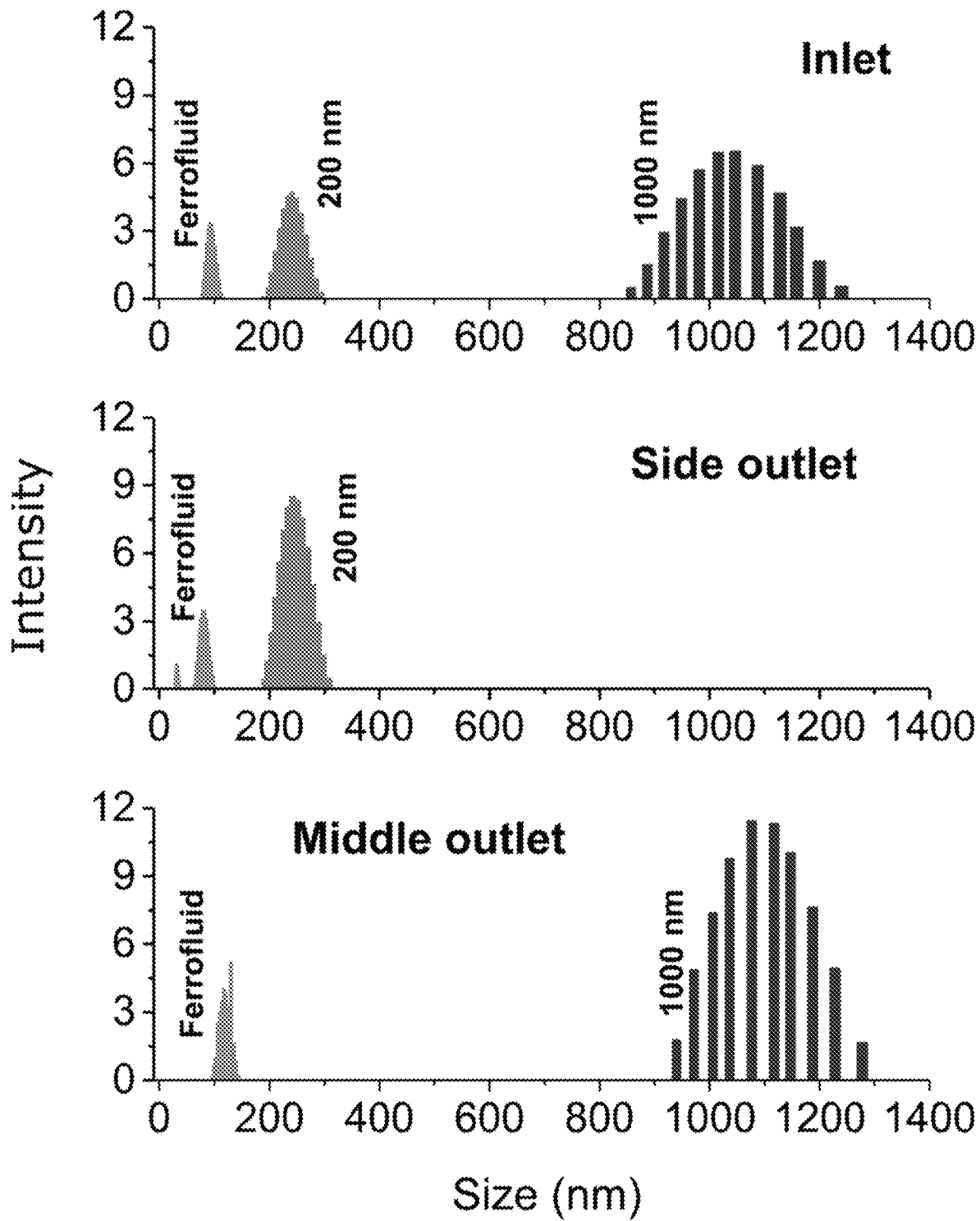
Figure 6:
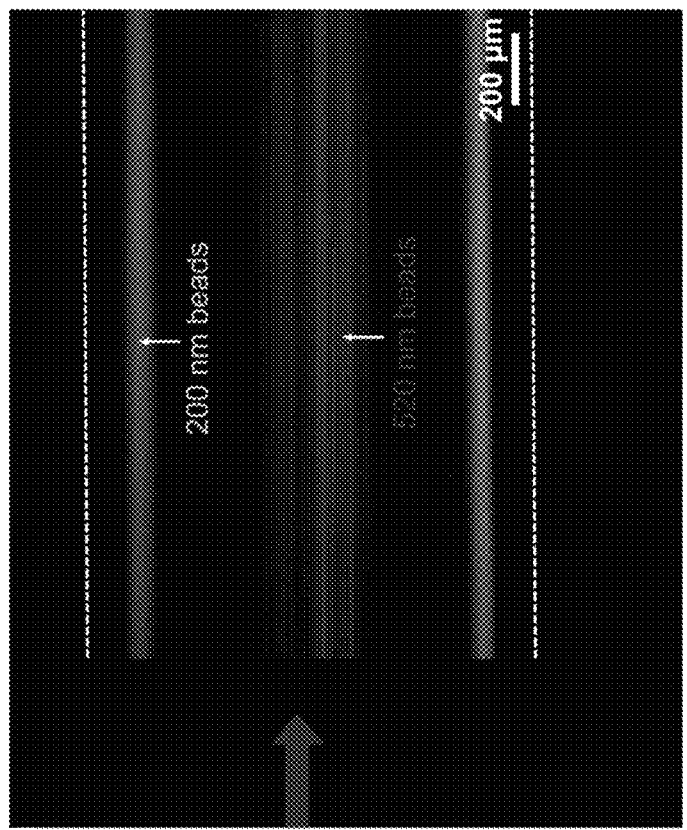
FIG. 6. illustrates simulation results vs/Experimental results of the separation of 200 nm and 520 nm polystyrene beads at different sample flow rates. The graph on the left illustrates a flow rate of (0-5 µL min$^{-1}$) in a 0.3% (v/v) ferrofluid in the FerroChip. The ratio of particle flow and sheath flow was 1:5 (sample—1 µL min$^{-1}$; sheath—5 µL min$^{-1}$). The image on the right shows experimental results of beads separation (green: 200 nm beads, red: 520 nm beads) at the end of the separation region in the FerroChip when the sample flow rate was 1 µL/min and sheath flow rate was 5 µL/min.
Figure 6:
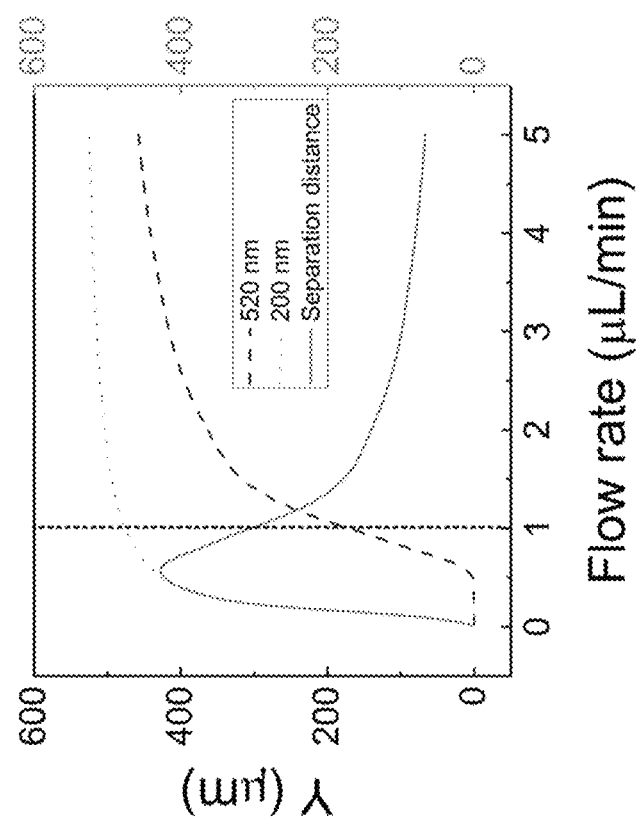

Using optimized device geometry and operating parameters, FerroChip's performance in separating 200 nm diamagnetic nanoparticles from a mixture of 200 nm and 1000 nm particles was evaluated. A typical separation device and process can be visualized in FIG. 4B, in which premixed blue fluorescent 200 nm diamagnetic particles and red fluorescent 1000 nm diamagnetic particles with 1 to 1 ratio were processed in a FerroChip device at a sample flow rate of 3 µL min$^{-1}$ and a sheath flow rate of 15 µL min$^{-1}$. Fluorescent images from the separation process show that before ferrohydrodynamic separation, both 200 nm and 1000 nm particles were mixed and remained close to the sidewall of the microchannel (observation windows 1, 2 and 3 in FIG. 4B). After ferrohydrodynamic separation, blue 200 nm particles migrated slightly away from the sidewall due to a weak ferrohydrodynamic effect on them and exited the channel through the side outlets. On the other hand, red 1000 nm particles experienced a significantly larger ferrohydrodynamic effect and migrated to the center of the channel and exited through the middle outlet (observation windows 4 and 5 in FIG. 4B). This experimental result matched the simulation result in FIG. 4A very well. From the fluorescent image analysis, it was confirmed that 200 nm particles could be recovered at 100% recovery rate from the side outlets, and the purity of 200 nm particles from the side outlets were 100% as none of the larger 1000 nm particles exited through side outlets. This result was further confirmed by collecting samples from FerroChip outlets and characterizing their particle size distribution using dynamic light scattering (DLS). FIG. 4C shows that the particle sample from the FerroChip inlet was a mixture of 200 nm and 1000 nm particles; samples collected from the side outlet were exclusively 200 nm particles; and samples collected from the middle outlet were exclusively 1000 nm particles. It was noted that maghemite particles in ferrofluids appeared in inlets and outlets too. The mean diameters of maghemite particles (~100 nm) from these spectra were larger than individual maghemite particles (~10 nm), likely due to particle agglomeration induced by the dilution process that disrupted the surfactant concentration. Additional simulation and experimental data of 200 nm and 520 nm diamagnetic particles in the supplementary information (FIG. 6) shows these two could be separated in the FerroChip as well. The theoretical size resolution of the FerroChip in separating nanoparticles was also studied and was found to be ~100 nm (FIGS. 7A-7C).

In summary, this Example showed that the performance of FerroChip devices in separating 200 nm and 1000 nm particles met or exceeded the goals, including: (1) a complete 200 nm particle recovery rate of 100%; (2) a sample processing throughput of 3 µL min$^{-1}$ (180 µL h$^{-1}$), and (3) a purity of 200 nm particles of 100% after separation. This performance enabled continued device characterization using biological samples. It is noted that the particles used in this experiment had a very narrow size distribution, which led to better-than-expected recovery rate and purity performance. When dealing with exosomes and other EVs in biological samples, their size polydispersity will lead to a decrease in the exosomal recovery rate and purity.

Validation of FerroChip for Exosome-Like Nanoparticles Separation Using Biological Samples.

The FerroChip's performance in separating exosomes from biological samples was characterized. The device geometry and operating parameters remained the same as in the experiments described above, except the sample flow rate was further decreased to 1 µL min$^{-1}$ (60 µL hour$^{-1}$) to maximize the separation between exosomes and large EVs (see FIG. 6). This was determined after considering the polydispersity of sizes of exosomes and large EVs.

Figure 5A:
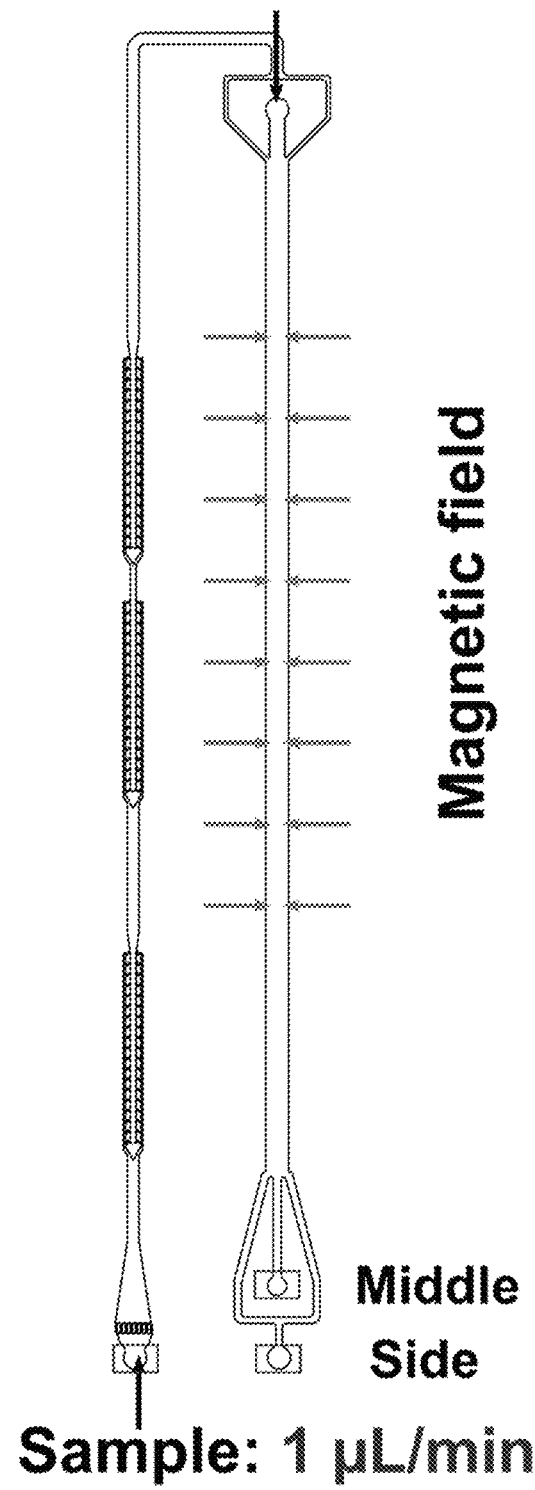
FIGS. 5A-5G characterize the FerroChip in separating exosome-like nanoparticles from biological samples.
Figure 5B:
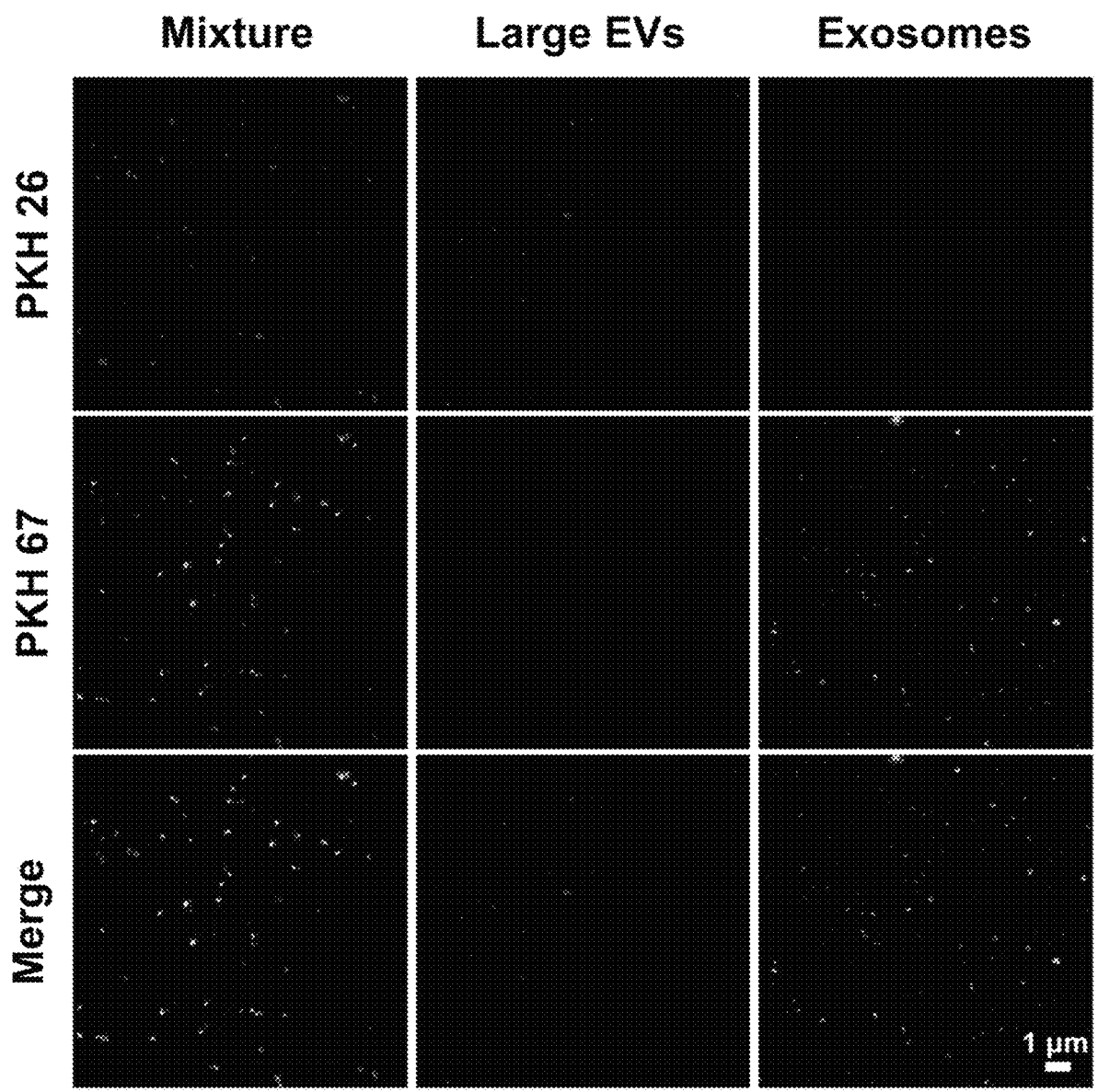
Figure 8:
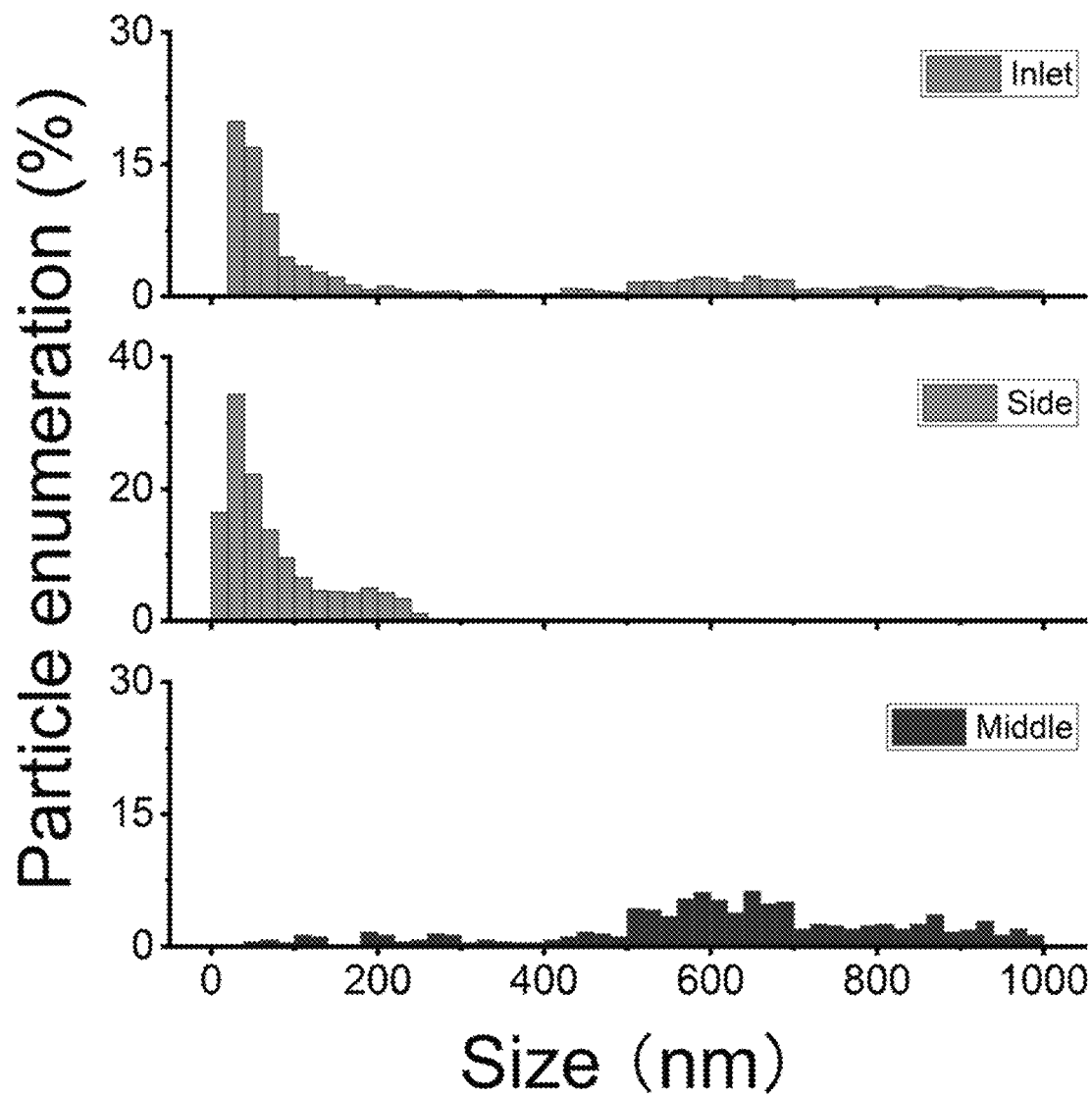
FIG. 8 is a series of graphs illustrating size distribution of extracellular vesicles (EVs) from MDA-MB-231 breast cancer cell culture media before and after the FerroChip processing. Y-axis is the EV enumeration and X-axis is the diameter of the EVs. Diameters of EVs were determined from atomic force microscopy. Before the FerroChip processing, 1650 EVs were counted from the inlet of the FerroChip, which showed a first peak between 0-100 nm and a second peak at ~600 nm. After processing, 1059 EVs were counted from the side outlets of the FerroChip, which showed a peak between 0-100 nm; 532 EVs were counted from the middle outlet, which showed a peak at ~600 nm.

The FerroChip was first challenged with extracellular media collected from cultured breast cancer cell line MDA-MB-231, and the exosomal recovery rate and purity of the FerroChip was characterized. The EVs from this media were first enriched and separated into two groups based on their sizes using ultracentrifugation and a commercial kit (ExoQuick-TC, see Materials and Methods). The first group contained large EVs (diameters: 200 nm to 1000 nm) that were stained with PKH 26 red fluorescence, and the second group contained small exosomes (diameters: 30 nm to 150 nm) that were stained with PKH 67 green fluorescence. Size profiles of the exosomes and large EVs were measured by atomic force microscopy and provided in FIG. 8. These two groups of EVs were then mixed together at a ratio of 1 to 1 (20 µL large EVs and 20 µL of exosomes resuspended in 1 mL of ferrofluids) and processed using the FerroChip at a sample flow rate of 1 µL min$^{-1}$ and a sheath flow rate of 5 µL min$^{-1}$ (FIG. 5A). After device processing, samples collected from middle and side outlets were analyzed for exosomal recovery and purity using two methods including super-resolution imaging and atomic force microscopy. In these analyses, exosome-like nanoparticles were defined to have diameters of 30-150 nm, and morphology and protein expressions consistent with other reports.[5] Firstly, from a super-resolution imaging analysis of 730 particles, the recovery rate of exosome-like particles, defined as the number of PKH 67 green fluorescent particles found in the side outlets over the number of PKH 67 green fluorescent particles found in all outlets of the FerroChip, was 92.6%, and the purity of recovered exosome-like particles, defined as the number of PKH 67 green fluorescent particles found in the side outlets over the sum of PKH 67 green fluorescent particles and PKH 26 red fluorescent particles found in the side outlets of the FerroChip, was 91.1% (Table 2).

TABLE 2

Table 2. Summary of recovery rate and purity of exosome-like particles separated from MDA-MB-231 breast cancer cell culture media using the FerroChip.

|  | Recovery rate | Purity |
| --- | --- | --- |
| AFM (n = 1581) | 96.0% | 84.7% |
| Super-resolution microscopy (n = 730) | 92.6% | 91.1% |
| Average of the above two methods | 94.3% | 87.9% |

Figure 5C:
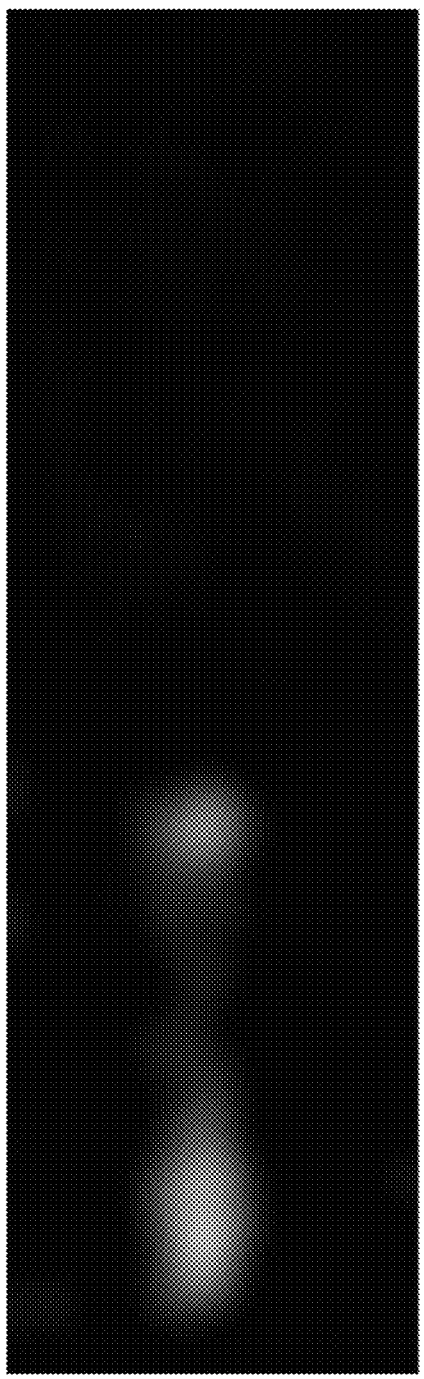
Figure 5C:
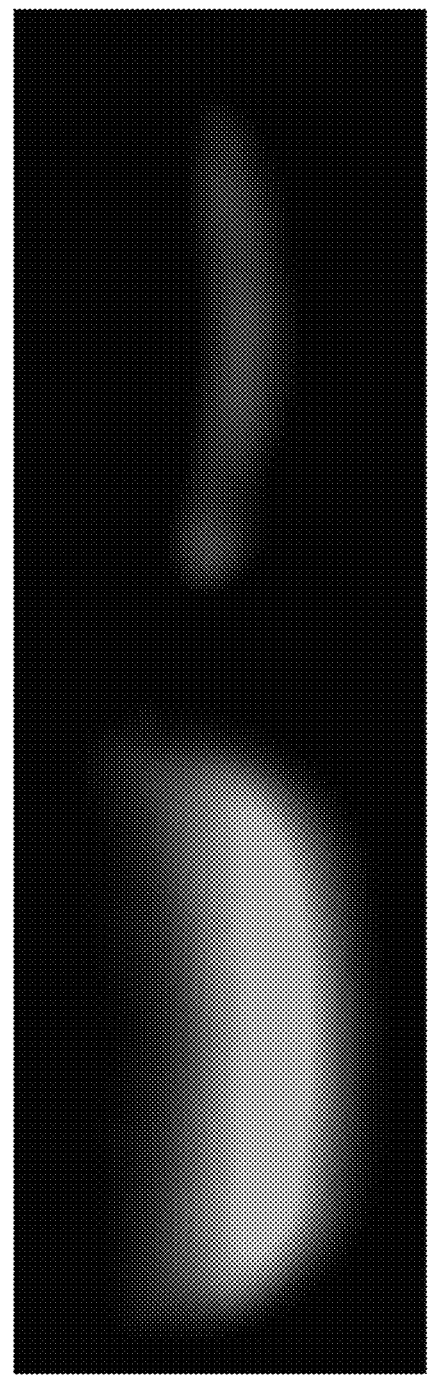
Figure 5D:
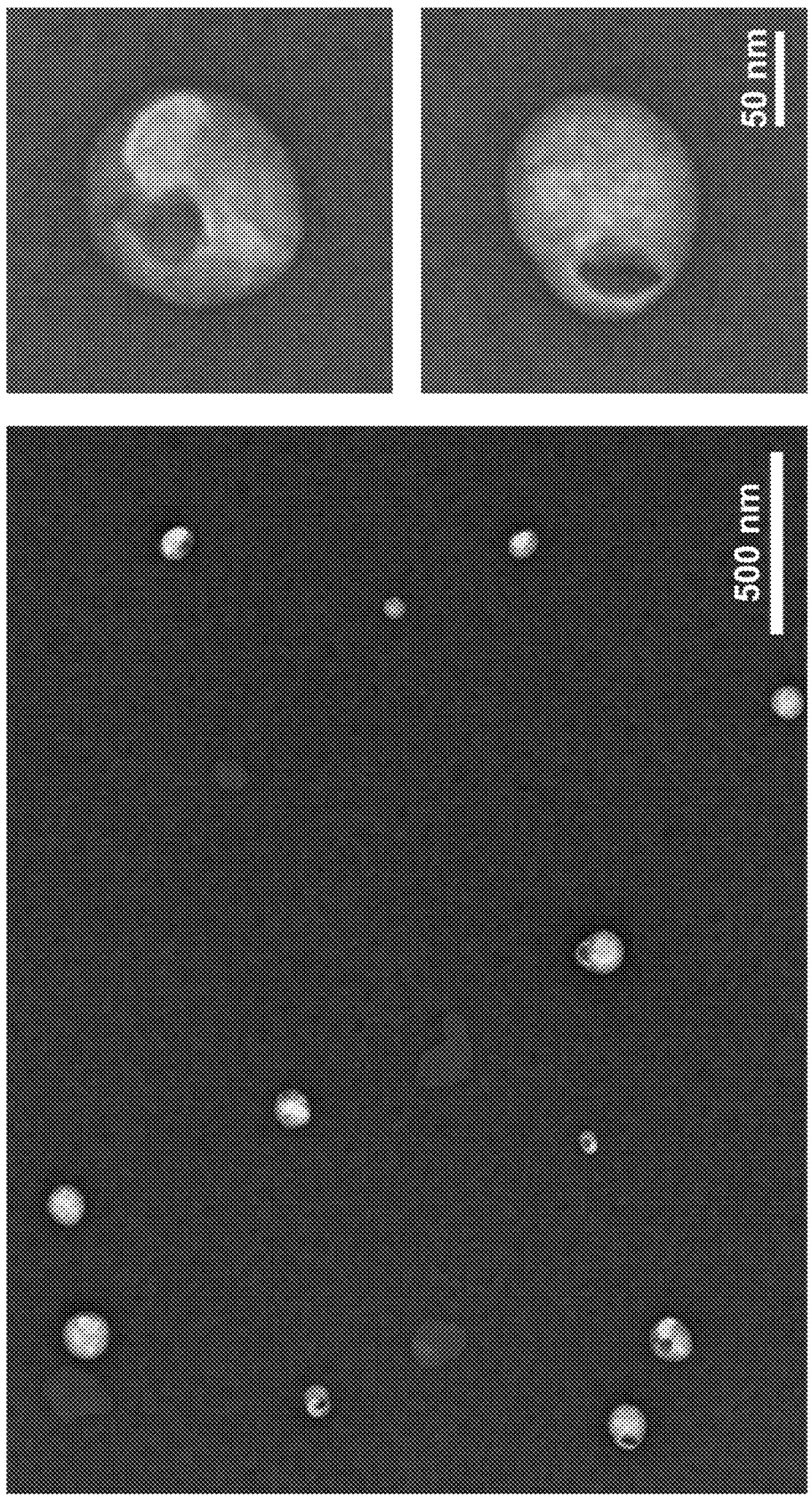
Figure 5E:
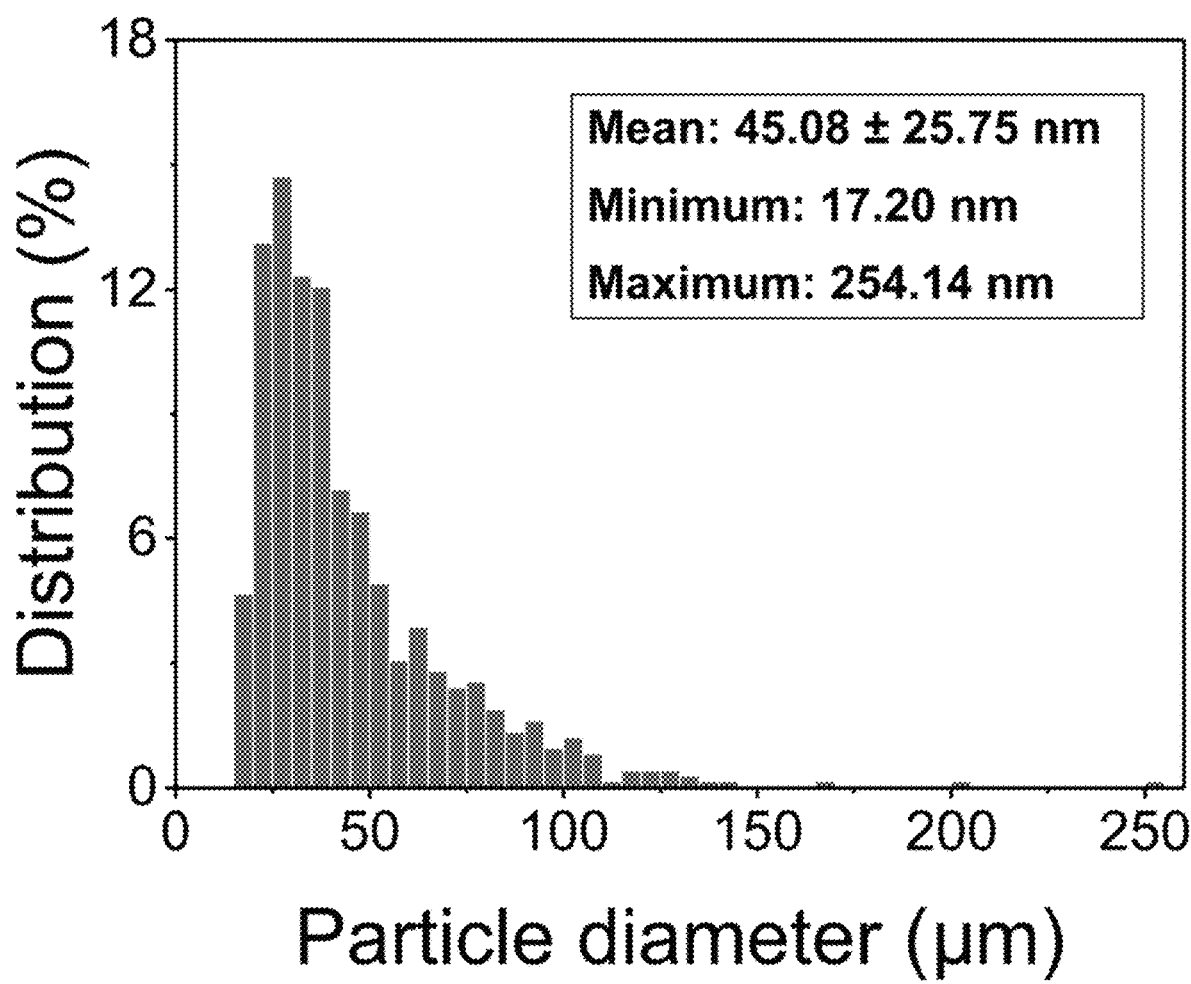
Figure 9:
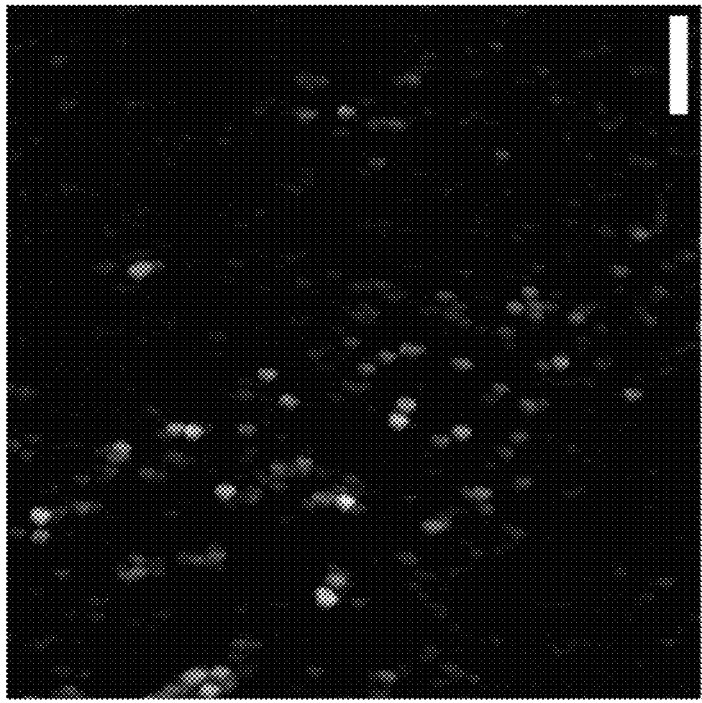
FIG. 9 is a pair of AFM images of extracellular vesicles (EVs) in the FerroChip separation experiment using MDA-MB-231 breast cancer cell culture media from FIGS. 5A-5E in the main text. AFM images of the sample before separation (left, mixture of exosomes and large EVs) and sample after separation (right, EVs collected from side outlet) showed a clear size difference. Sample flow rate is 1 µL min$^{-1}$, and sheath flow rate is 5 µL min$^{-1}$. Scale bar: 1 µm.
Figure 9:
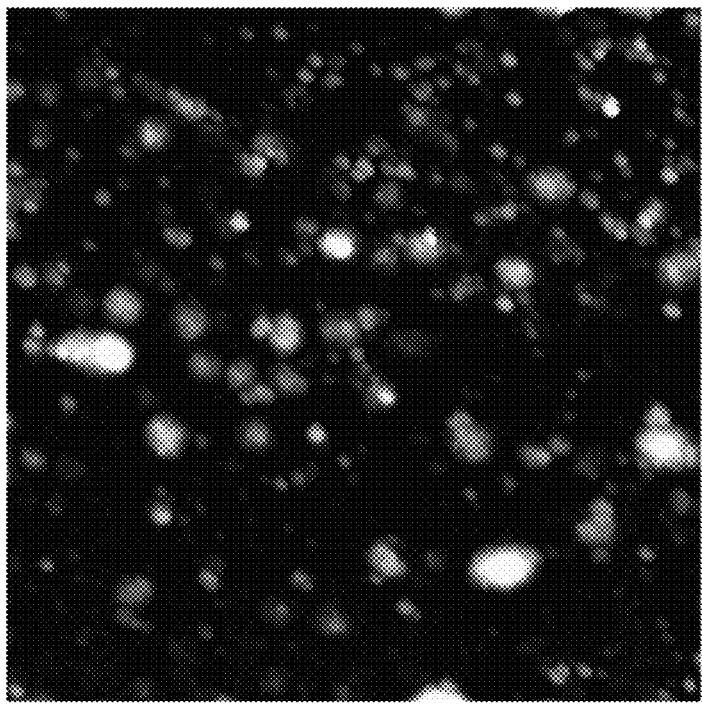

Secondly, the separation of the exosomes and large EVs was analyzed by atomic force microscopy (AFM, representative images in FIG. 9). From an atomic force microscopic image analysis of 1581 particles, we found that the recovery rate of exosome-like particles with diameter less than 150 nm was 96%, and the purity was 84.7% (Table 2). The average recovery rate between these two characterization methods was 94.3% and the average purity was 87.9%. In addition, transmission electron microscopy (TEM) was used to characterize the diameter distribution of the separated exosome-like particles from the FerroChip. FIG. 5E shows that the diameter distribution of these separated exosome-like nanoparticles was 45±26 nm, with a minimal diameter of 17 nm and a maximal diameter of 254 nm. This diameter range was consistent with established exosome diameters (30-150 nm).[5] Conventional transmission electron microscopy with negative staining of the exosome output from the FerroChip also revealed that most separated exosomes had an artifactual cup-shaped morphology caused by shrinking (FIG. 5D), consistent with their established morphology in literature.[5] Magnetic nanoparticles were removed from the exosome solution prior to the TEM. This process, described in Materials and Methods, did not appear to affect the morphology of the exosomes. Western blot analysis was used to examine the expression of exosomal protein markers in the samples collected from the side outlets and the middle outlet. Expression of EV membrane tetraspanin CD63 and heat shock 70 kDa protein, HSP70 was also analyzed. The sample collected from the side outlets showed a high expression of CD63 and HSP70 (FIG. 5C), confirming that the majority of exosomes were separated from the initial EV mixture into the side outlets. The EVs collected from the middle outlet showed a low level of CD63, indicating that a small quantity of exosomes also exited the device through the middle outlet. In addition to the separation of exosomes from the extracellular media, an effective focusing effect on EVs in the FerroChip was also demonstrated (see supplementary information FIG. 10).

Figure 5F:
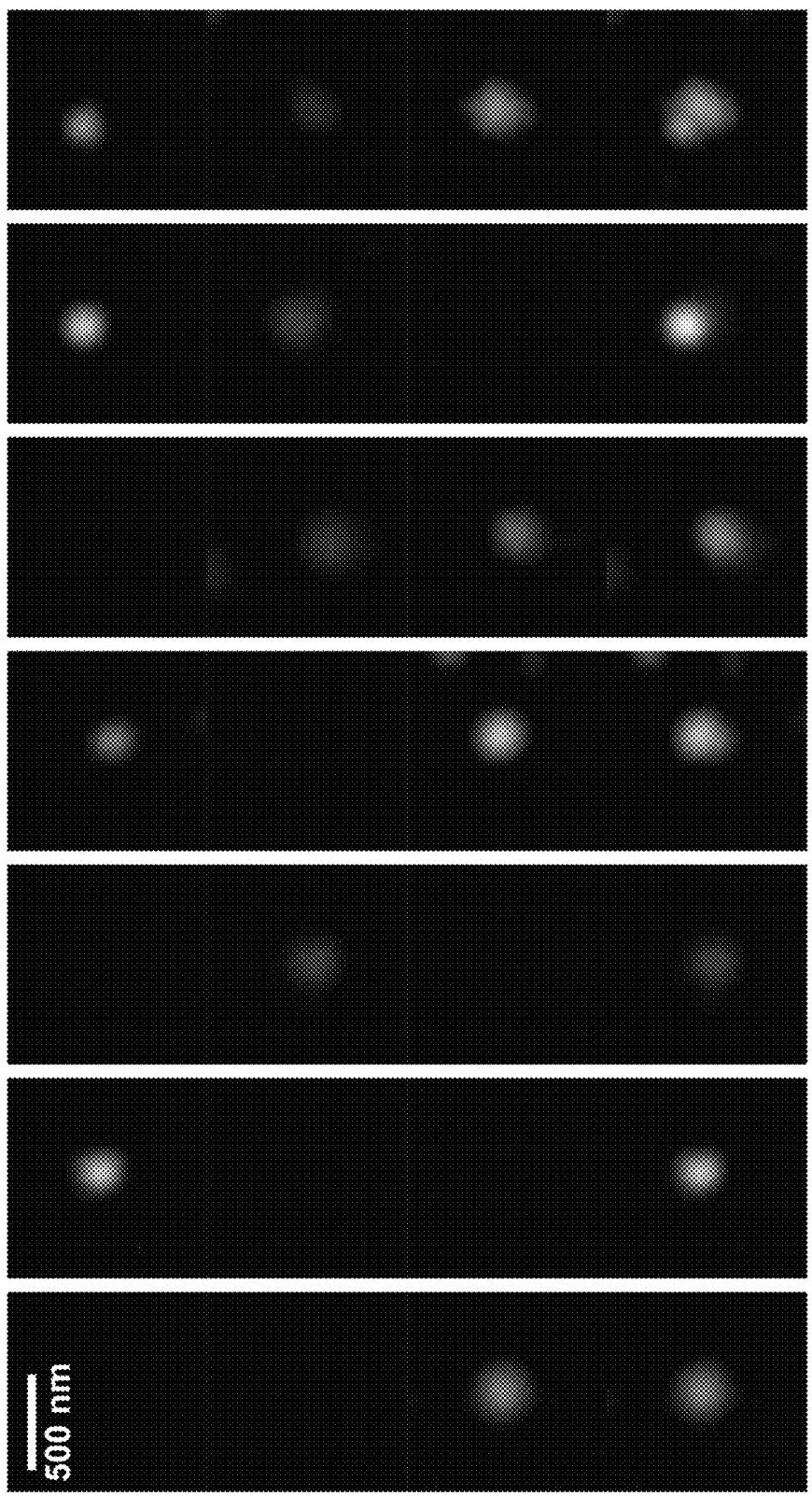
Figure 5G:
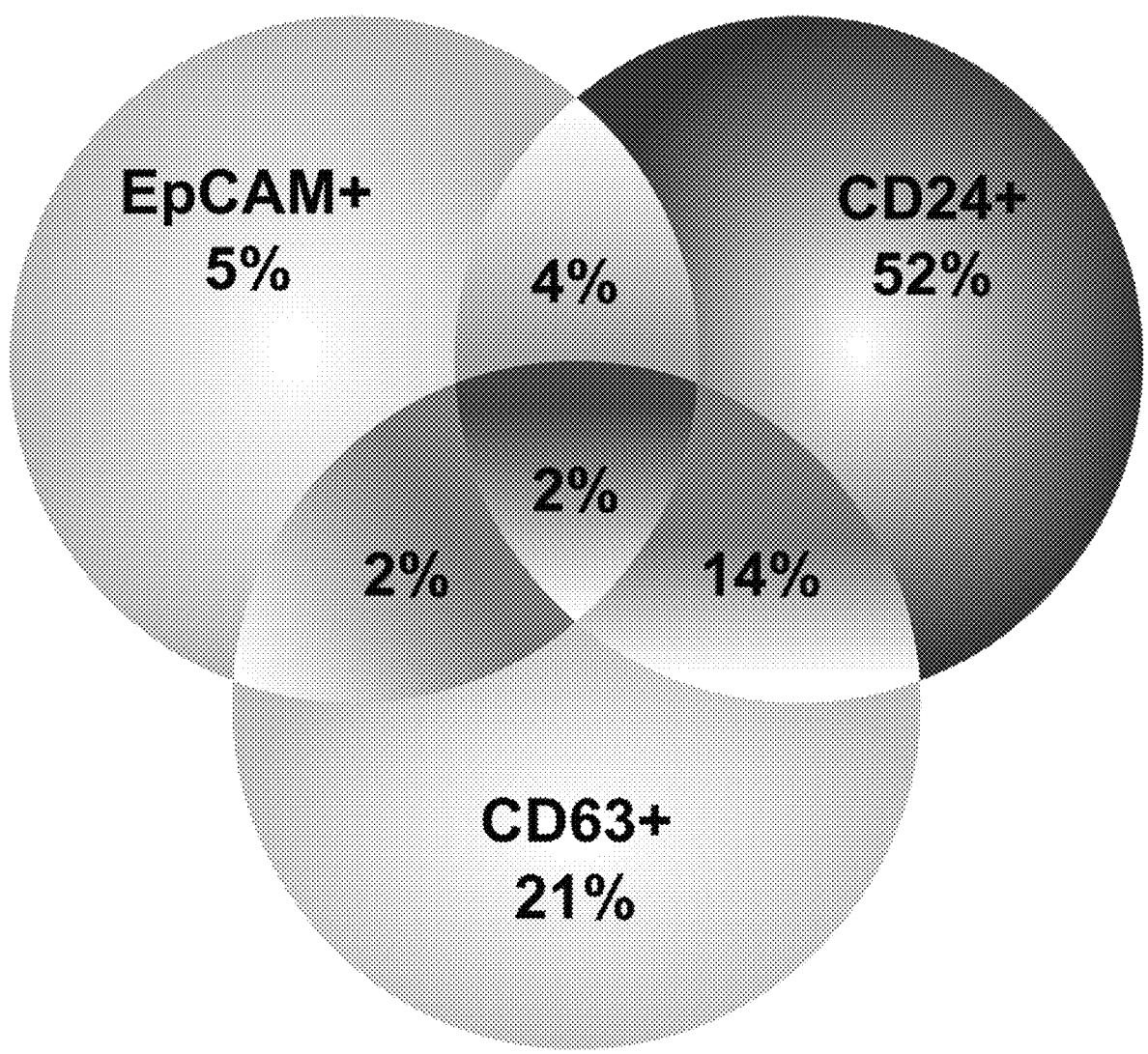
Figure 11:
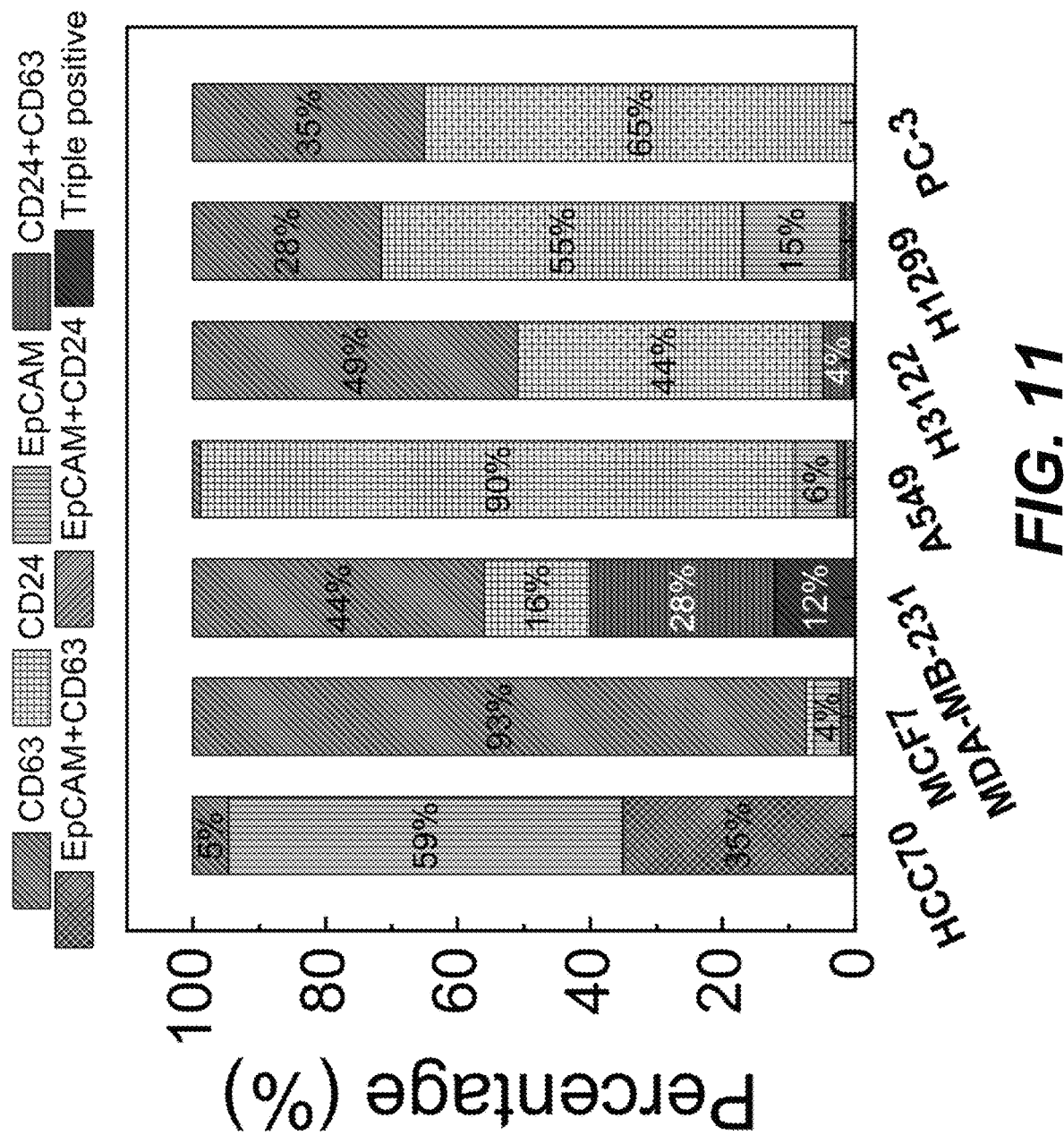
FIG. 11 illustrates the percentage of antibody presence on the surfaces of separated exosomes (n=1000) from the culture media of 7 cancer cell lines (breast cancer: HCC70, MCF7, MDA-MB-231; lung cancer: A549, H3122, H1299; prostate cancer: PC-3).

FerroChip was further challenged with serum from a healthy human's blood to show that the FerroChip could separate exosome-like nanoparticles from the serum. For this purpose, 100 µL of serum was processed using the FerroChip at a sample flow rate of 1 µL min$^{-1}$ and a sheath flow rate of 5 µL min$^{-1}$. Exosomes separated from the FerroChip were investigated for their molecular signatures through the profiling of three antibodies. These antibodies were chosen based on prior studies, including CD63 that was particularly enriched on the surface of exosomes,[5,26,36] and two putative cancer makers—epithelial cell adhesion molecule (EpCAM) and CD24.[26,36] Both of these cancer markers were not only detected in tumor-derived exosomes, but also in samples from healthy subjects.[26] All three markers, CD63, EpCAM, and CD24 were detected in different combinations on the exosomes' surface from the human serum (FIG. 5F). FIG. 5G shows the Venn diagram depicting the percentage of each antibody's presence—EpCAM+ alone:

5%; CD24+ alone: 52%; CD63+ alone: 21%; EpCAM+/CD24+:4%; EpCAM+/CD63+:2%; CD24+/CD63+:14%; CD63+/CD24+/EpCAM+:2%. FerroChip was also challenged with extracellular media from 7 cancer cell lines and investigated for antibody presence on the surfaces of recovered exosomes. The presence of these antibodies was heterogeneous across the cell lines (see supplementary information FIG. 11). This collective information indicates that using a label-based exosome separation strategy will result in partial recovery and highlights a need for label-free strategies include the FerroChip.

Advantages and Limitations of the FerroChip in Separating Exosome-Like Particles.

The FerroChip's performance of separating exosome-like nanoparticles was compared to existing microfluidic methods. In doing so, three metrics were used including the sample-processing throughput, exosomal particle recovery rate, and purity of recovered exosomes. These three metrics were well established in the current literature of exosome separation.[6,35] Through validations with both spike-in samples and biological samples using these operating parameters, the performance of the FerroChip in separating exosome-like particles was determined to have: (1) a recovery rate of 94.3%; (2) a purity of 87.9% in recovered particles; (3) a sample processing throughput of 60 µL h$^{-1}$. These results were compared to recently published microfluidic methods and found to have a better combined recovery rate and purity than existing methods.[17, 19, 27, 37-45]

However, the devices of the present disclosure tested in this example exhibit some limitations in separating exosome-like nanoparticles from biological fluids. For instance, the sample processing throughput of the FerroChip in this example was limited to ~60 µL h$^{-1}$. In the process of separating exosome-like particles from biological fluids, a sheath flow of ferrofluids was introduced along with the sample which resulted in a dilution of separated particles. For these reasons this FerroChip may be suited for applications such as blood liquid biopsy where the starting sample volume is typically small (~100 µL) and the tumor-derived exosomes are about >10$^9$/mL.[20, 26, 35, 46] Secondly, while previous studies have demonstrated the ferrofluids had minimally detrimental effects on mammalian cells,[31, 32, 47] and in this study, the biophysical diameter, morphology and common protein expressions appeared to be consistent with other reports, further molecular characterizations can assess the quality of the exosome-like particles from the FerroChip. Lastly, the FerroChip relies on the size-dependent ferrohydrodynamic force to separate larger EVs from smaller exosomes. As a result, it cannot distinguish exosomes from particulate impurities that have similar sizes in a biological fluid, which may lead to decreased purity of separated exosomes.

Conclusion

The present example provides a new label-free ferrohydrodynamic method and devices/kits (FerroChip) for a size-based separation of exosome-like particles from biological samples. FerroChip relies on particle ferrohydrodynamics of nanoscale extracellular vesicles in a biocompatible ferrofluid to focus heterogeneous populations of sub-micron/exosome-like particles to provide an enriched sample as well as to separate smaller exosome-like nanoparticles from larger extracellular vesicles (EVs). Particle ferrohydrodynamics developed in the past was limited to micron-sized particle and cellular separations. This successfully demonstrated both in theory and with experiments that particle ferrohydrodynamics could be applied to exosome-like nanoparticles separation in microfluidic devices with ~100 nm size resolution. The developed FerroChip was used to separate exosome-like nanoparticles, defined as particles of 30-150 nm and having morphology and protein markers that were consistent exosomes, from biological fluids. FerroChip's separation had a recovery rate of 94.3% and a purity of 87.9% in recovered exosome-like nanoparticles. This is believed to be the first instance and description of separation of nanosized particles via particle ferrohydrodynamics in microfluidic devices.

REFERENCES

1. J. Massague and A. C. Obenauf, Nature, 2016, 529, 298-306.
2. A. W. Lambert, D. R. Pattabiraman and R. A. Weinberg, Cell, 2017, 168, 670-691.
3. E. T. Roussos, J. S. Condeelis and A. Patsialou, Nat Rev Cancer, 2011, 11, 573-587.
4. R. Xu, A. Rai, M. Chen, W. Suwakulsiri, D. W. Greening and R. J. Simpson, Nat Rev Clin Oncol, 2018, 15, 617-638.
5. G. van Niel, G. D'Angelo and G. Raposo, Nat Rev Mol Cell Biol, 2018, 19, 213-228.
6. J. C. Contreras-Naranjo, H. J. Wu and V. M. Ugaz, Lab Chip, 2017, 17, 3558-3577.
7. M. Mathieu, L. Martin-Jaular, G. Lavieu and C. Thery, Nat Cell Biol, 2019, 21, 9-17.
8. H. Peinado, H. Zhang, I. R. Matei, B. Costa-Silva, A. Hoshino, G. Rodrigues, B. Psaila, R. N. Kaplan, J. F. Bromberg, Y. Kang, M. J. Bissell, T. R. Cox, A. J. Giaccia, J. T. Erler, S. Hiratsuka, C. M. Ghajar and D. Lyden, Nat Rev Cancer, 2017, 17, 302-317.
9. T. Celia-Terrassa and Y. Kang, Nat Cell Biol, 2018, 20, 868-877.
10. B. Costa-Silva, N. M. Aiello, A. J. Ocean, S. Singh, H. Zhang, B. K. Thakur, A. Becker, A. Hoshino, M. T. Mark, H. Molina, J. Xiang, T. Zhang, T. M. Theilen, G. Garcia-Santos, C. Williams, Y. Ararso, Y. Huang, G. Rodrigues, T. L. Shen, K. J. Labori, I. M. Lothe, E. H. Kure, J. Hernandez, A. Doussot, S. H. Ebbesen, P. M. Grandgenett, M. A. Hollingsworth, M. Jain, K. Mallya, S. K. Batra, W. R. Jarnagin, R. E. Schwartz, I. Matei, H. Peinado, B. Z. Stanger, J. Bromberg and D. Lyden, Nat Cell Biol, 2015, 17, 816-826.
11. B. A. Aguado, G. G. Bushnell, S. S. Rao, J. S. Jeruss and L. D. Shea, Nat Biomed Eng, 2017, 1.
12. H. Peinado, M. Aleckovic, S. Lavotshkin, I. Matei, B. Costa-Silva, G. Moreno-Bueno, M. Hergueta-Redondo, C. Williams, G. Garcia-Santos, C. Ghajar, A. Nitadori-Hoshino, C. Hoffman, K. Badal, B. A. Garcia, M. K. Callahan, J. Yuan, V. R. Martins, J. Skog, R. N. Kaplan, M. S. Brady, J. D. Wolchok, P. B. Chapman, Y. Kang, J. Bromberg and D. Lyden, Nat Med, 2012, 18, 883-891.
13. A. Hoshino, B. Costa-Silva, T. L. Shen, G. Rodrigues, A. Hashimoto, M. Tesic Mark, H. Molina, S. Kohsaka, A. Di Giannatale, S. Ceder, S. Singh, C. Williams, N. Soplop, K. Uryu, L. Pharmer, T. King, L. Bojmar, A. E. Davies, Y. Ararso, T. Zhang, H. Zhang, J. Hernandez, J. M. Weiss, V. D. Dumont-Cole, K. Kramer, L. H. Wexler, A. Narendran, G. K. Schwartz, J. H. Healey, P. Sandstrom, K. J. Labori, E. H. Kure, P. M. Grandgenett, M. A. Hollingsworth, M. de Sousa, S. Kaur, M. Jain, K. Mallya, S. K. Batra, W. R. Jarnagin, M. S. Brady, O. Fodstad, V. Muller, K. Pantel, A. J. Minn, M. J. Bissell, B. A. Garcia, Y. Kang, V. K. Rajasekhar, C. M. Ghajar, I. Matei, H. Peinado, J. Bromberg and D. Lyden, Nature, 2015, 527, 329-335.

14. H. Shao, J. Chung, K. Lee, L. Balaj, C. Min, B. S. Carter, F. H. Hochberg, X. O. Breakefield, H. Lee and R. Weissleder, *Nat Commun,* 2015, 6, 6999.

15. C. Chen, J. Skog, C. H. Hsu, R. T. Lessard, L. Balaj, T. Wurdinger, B. S. Carter, X. O. Breakefield, M. Toner and D. Irimia, *Lab Chip,* 2010, 10, 505-511.

16. B. A. Ashcroft, J. de Sonneville, Y. Yuana, S. Osanto, R. Bertina, M. E. Kuil and T. H. Oosterkamp, *Biomed Microdevices,* 2012, 14, 641-649.

17. S. S. Kanwar, C. J. Dunlay, D. M. Simeone and S. Nagrath, *Lab on a Chip,* 2014, 14, 1891-1900.

18. H. Im, H. L. Shao, Y. I. Park, V. M. Peterson, C. M. Castro, R. Weissleder and H. Lee, *Nat Biotechnol,* 2014, 32, 490-U219.

19. P. Zhang, M. He and Y. Zeng, *Lab on a Chip,* 2016, 16, 3033-3042.

20. Y. Wan, G. Cheng, X. Liu, S. J. Hao, M. Nisic, C. D. Zhu, Y. Q. Xia, W. Q. Li, Z. G. Wang, W. L. Zhang, S. J. Rice, A. Sebastian, I. Albert, C. P. Belani and S. Y. Zheng, *Nat Biomed Eng,* 2017, 1.

21. B. H. Wunsch, J. T. Smith, S. M. Gifford, C. Wang, M. Brink, R. L. Bruce, R. H. Austin, G. Stolovitzky and Y. Astier, *Nat Nanotechnol,* 2016, 11, 936-940.

22. S. Shin, D. Han, M. C. Park, J. Mun, J. Choi, H. Chun, S. Kim and J. W. Hong, *Sci Rep-Uk,* 2017, 7.

23. H. Zhang and D. Lyden, *Nat Protoc,* 2019, 14, 1027-1053.

24. F. Liu, 0. Vermesh, V. Mani, T. J. Ge, S. J. Madsen, A. Sabour, E. C. Hsu, G. Gowrishankar, M. Kanada, J. V. Jokerst, R. G. Sierra, E. Chang, K. Lau, K. Sridhar, A. Bermudez, S. J. Pitteri, T. Stoyanova, R. Sinclair, V. S. Nair, S. S. Gambhir and U. Demirci, *ACS Nano,* 2017, 11, 10712-10723.

25. Z. Wang, H. J. Wu, D. Fine, J. Schmulen, Y. Hu, B. Godin, J. X. Zhang and X. Liu, *Lab Chip,* 2013, 13, 2879-2882.

26. P. Zhang, X. Zhou, M. He, Y. Shang, A. L. Tetlow, A. K. Godwin and Y. Zeng, *Nat Biomed Eng,* 2019, 3, 438-451.

27. C. Liu, J. Guo, F. Tian, N. Yang, F. Yan, Y. Ding, J. Wei, G. Hu, G. Nie and J. Sun, *ACS Nano,* 2017, 11, 6968-6976.

28. M. Wu, Y. Ouyang, Z. Wang, R. Zhang, P. H. Huang, C. Chen, H. Li, P. Li, D. Quinn, M. Dao, S. Suresh, Y. Sadovsky and T. J. Huang, *Proc Natl Acad Sci U S A,* 2017, 114, 10584-10589.

29. R. E. Rosensweig, *Ferrohydrodynamics*, Cambridge University Press, Cambridge, 1985.

30. W. Zhao, R. Cheng, J. R. Miller and L. Mao, *Adv Funct Mater,* 2016, 26, 3916-3932.

31. W. J. Zhao, R. Cheng, B. D. Jenkins, T. T. Zhu, N. E. Okonkwo, C. E. Jones, M. B. Davis, S. K. Kavuri, Z. L. Hao, C. Schroeder and L. D. Mao, *Lab on a Chip,* 2017, 17, 3097-3111.

32. W. Zhao, Y. Liu, B. D. Jenkins, R. Cheng, B. N. Harris, W. Zhang, J. Xie, J. R. Murrow, J. Hodgson, M. Egan, A. Bankey, P. G. Nikolinakos, H. Y. Ali, K. Meichner, L. A. Newman, M. B. Davis and L. Mao, *Lab Chip,* 2019, 19, 1860-1876.

33. R. M. Erb, H. S. Son, B. Samanta, V. M. Rotello and B. B. Yellen, *Nature,* 2009, 457, 999-1002.

34. T. Zhu, R. Cheng, S. A. Lee, E. Rajaraman, M. A. Eiteman, T. D. Querec, E. R. Unger and L. Mao, *Microfluid Nanofluidics,* 2012, 13, 645-654.

35. M. He and Y. Zeng, Jala-J *Lab Autom,* 2016, 21, 599-608.

36. H. Im, H. Shao, Y. I. Park, V. M. Peterson, C. M. Castro, R. Weissleder and H. Lee, *Nat Biotechnol,* 2014, 32, 490-495.

37. B. Ashcroft, J. De Sonneville, Y. Yuana, S. Osanto, R. Bertina, M. Kuil and T. Oosterkamp, *Biomed Microdevices,* 2012, 14, 641-649.

38. C. Chen, J. Skog, C.-H. Hsu, R. T. Lessard, L. Balaj, T. Wurdinger, B. S. Carter, X. O. Breakefield, M. Toner and D. Irimia, *Lab on a Chip,* 2010, 10, 505-511.

39. H. Im, H. Shao, Y. I. Park, V. M. Peterson, C. M. Castro, R. Weissleder and H. Lee, *Nature biotechnology,* 2014, 32, 490.

40. H. Shao, J. Chung, K. Lee, L. Balaj, C. Min, B. S. Carter, F. H. Hochberg, X. O. Breakefield, H. Lee and R. Weissleder, *Nature communications,* 2015, 6, 1-9.

41. S. Shin, D. Han, M. C. Park, J. Y. Mun, J. Choi, H. Chun, S. Kim and J. W. Hong, *Sci Rep-Uk,* 2017, 7, 1-8.

42. Z. Wang, H.-j. Wu, D. Fine, J. Schmulen, Y. Hu, B. Godin, J. X. Zhang and X. Liu, *Lab on a Chip,* 2013, 13, 2879-2882.

43. M. Wu, Y. Ouyang, Z. Wang, R. Zhang, P.-H. Huang, C. Chen, H. Li, P. Li, D. Quinn and M. Dao, *Proceedings of the National Academy of Sciences,* 2017, 114, 10584-10589.

44. B. H. Wunsch, J. T. Smith, S. M. Gifford, C. Wang, M. Brink, R. L. Bruce, R. H. Austin, G. Stolovitzky and Y. Astier, *Nature nanotechnology,* 2016, 11, 936.

45. H. Zhang and D. Lyden, *Nature protocols,* 2019, 14, 1027-1053.

46. H. Xu, C. Liao, P. Zuo, Z. Liu and B. C. Ye, *Anal Chem,* 2018, 90, 13451-13458.

47. W. J. Zhao, R. Cheng, S. H. Lim, J. R. Miller, W. Z. Zhang, W. Tang, J. Xie and L. D. Mao, *Lab on a Chip,* 2017, 17, 2243-2255.

We claim at least the following:

1. A method of enriching and/or sorting unlabeled, sub-micron size particles in a sample comprising a plurality of components, the method comprising:

introducing a mixed sample fluid comprising the sample with the unlabeled, sub-micron size particles and a first ferrofluid into a first fluid inlet at a first end of a microfluidic channel of a multi-stage microfluidic device at a first flow rate, wherein the unlabeled, sub-micron size particles comprise a first and second sub-population of particles, wherein an average diameter of particles in the first sub-population of particles is larger than an average diameter of particles in the second sub-population of particles;

filtering large debris from the mixed sample fluid in a first stage of the device after the first inlet and comprising a filter region having one or more filters configured to separate at least a portion of larger debris from the mixed sample fluid;

introducing a sheathing ferrofluid into a second fluid inlet of the microfluidic device at a second flow rate, wherein the second fluid inlet is after the filter region and positioned and configured to introduce a sheathing ferrofluid along a center longitudinal axis of the microfluidic channel at a second flow rate, wherein the first ferrofluid and the sheathing ferrofluid each comprise a plurality of magnetic nanoparticles, a surfactant and a carrier fluid, and wherein the sheathing ferrofluid has a volume concentration of magnetic nanoparticles that is about 50% to 90% of the volume concentration of magnetic nanoparticles in the mixed sample fluid;

and flowing the mixed sample fluid and sheathing ferrofluid through a second stage of the device, the second stage located after the second fluid inlet and comprising a magnetic source configured to produce a substantially symmetric magnetic field having a field minimum along an inner longitudinal axis of the microfluidic channel and sufficient to cause the unlabeled sub-micron sized particles to be focused toward a center of the microfluidic channel of the second stage as a function of the size of the particles such that sheath flow of the sheathing ferrofluid in combination with the substantially symmetric magnetic field produced by the magnetic force in the second stage hydrodynamically focuses the unlabeled sub-micron sized particles in the mixed sample fluid to move toward a center of the microfluidic channel of the second stage as a function of particle size, such that the particles in the first sub-population of particles are more focused toward a center of the microfluidic channel of the second stage than the second sub-population of particles, such that a majority of the first sub-population of particles flow along a center of the microfluidic channel toward a first outlet at a second end of the microfluidic channel and positioned to receive unlabeled sub-micron sized particles in fluid flowing along a center of the microfluidic channel and a majority of the second sub-population of particles flows along the periphery of the microfluidic channel toward a second outlet at the second end of the microfluidic channel, the second outlet having at least one opening positioned to receive unlabeled sub-micron sized particles in fluid flowing along a periphery of the microfluidic channel.

2. The method according to claim 1, wherein the sample is a biological sample selected from the group consisting of: blood plasma, extracellular fluid, and blood that has been processed to remove blood cells, wherein the biological sample comprises a plurality of components.

3. The method of claim 1, wherein at least one of the first or second sub-population of sub-micron sized particles are exosomes.

4. The method of claim 1, wherein the mixed fluid sample has a first flow rate and the sheathing ferrofluid has a second flow rate and wherein the ratio of the first flow rate to the second flow rate is about 1:3 to 1:10.

5. The method of claim 1, wherein the flow rate of the fluid sample at the first inlet is about 0.01-20 uL/min.

6. The method of claim 1, wherein the flow rate of sheathing fluid is about 0.03-200 µL/min.

7. The method of claim 1, wherein the flow rate of the mixed sample fluid is about 1 µL/min and flow rate of sheathing fluid is about 3-10 L/min.

8. The method of claim 1, wherein the mixed sample fluid has a concentration of magnetic nanoparticles of about 0.01% to 0.6% (v/v).

* * * * *

UNITED STATES PATENT AND TRADEMARK OFFICE
CERTIFICATE OF CORRECTION

Page 1 of 1

PATENT NO. : 11,841,365 B2
APPLICATION NO. : 16/930664
DATED : December 12, 2023
INVENTOR(S) : Leidong Mao, Yang Liu and Wujun Zhao It is certified that error appears in the above-identified patent and that said Letters Patent is hereby corrected as shown below:

On the Title Page

(72) Inventors should read:
--Leidong Mao, Watkinsville, GA (US)
Yang Liu, Athens, GA (US)
Wujun Zhao, Waunakee, WI (US)--

Signed and Sealed this
Fourteenth Day of May, 2024

Katherine Kelly Vidal
*Director of the United States Patent and Trademark Office*